(12) United States Patent
Fujikado et al.

(10) Patent No.: US 10,959,615 B2
(45) Date of Patent: Mar. 30, 2021

(54) EYE-FATIGUE EXAMINING DEVICE AND EYE-FATIGUE EXAMINING METHOD

(71) Applicants: OSAKA UNIVERSITY, Osaka (JP); TOPCON CORPORATION, Tokyo (JP)

(72) Inventors: Takashi Fujikado, Osaka (JP); Masakazu Hirota, Osaka (JP); Kohji Nishida, Osaka (JP); Makoto Saika, Tokyo (JP); Tatsuo Yamaguchi, Tokyo (JP); Suguru Miyagawa, Tokyo (JP)

(73) Assignees: TOPCON CORPORATION, Tokyo (JP); OSAKA UNIVERSITY, Osaka (JP)

( * ) Notice: Subject to any disclaimer, the term of this patent is extended or adjusted under 35 U.S.C. 154(b) by 163 days.

(21) Appl. No.: 16/085,595

(22) PCT Filed: Feb. 20, 2017

(86) PCT No.: PCT/JP2017/006177
§ 371 (c)(1),
(2) Date: Sep. 17, 2018

(87) PCT Pub. No.: WO2017/159225
PCT Pub. Date: Sep. 21, 2017

(65) Prior Publication Data
US 2019/0099076 A1    Apr. 4, 2019

(30) Foreign Application Priority Data

Mar. 18, 2016 (JP) .............................. JP2016-055553

(51) Int. Cl.
*A61B 3/113* (2006.01)
*A61B 3/10* (2006.01)
(Continued)

(52) U.S. Cl.
CPC ............ *A61B 3/113* (2013.01); *A61B 3/0008* (2013.01); *A61B 3/0016* (2013.01); *A61B 3/08* (2013.01); *A61B 3/10* (2013.01)

(58) Field of Classification Search
CPC ......... A61B 3/08; A61B 3/113; A61B 3/0008; A61B 3/10; A61B 3/085; A61B 3/14
See application file for complete search history.

(56) References Cited

U.S. PATENT DOCUMENTS 5,094,521 A * 3/1992 Jolson ................ A61B 3/085
351/206
5,530,492 A * 6/1996 Ron ................... A61B 3/032
348/54
(Continued)

FOREIGN PATENT DOCUMENTS

JP    S60253429 A    12/1985
JP    2003070740 A    3/2003
(Continued)

OTHER PUBLICATIONS

English-language translation of International Search Report and Written Opinion for International Application No. PCT/JP2017/006177, dated May 16, 2017.
(Continued)

*Primary Examiner* — Christopher Stanford
(74) *Attorney, Agent, or Firm* — Xsensus LLP

(57) ABSTRACT

An eye-fatigue examining device and an eye-fatigue examining method capable of examining eye fatigue of a subject's eye regardless of an age of a patient are provided. The eye-fatigue examining device includes: a light quantity difference adjusting unit that increases a light quantity difference between lights respectively incident on right and left subject's eyes; a gaze direction detecting unit that detects gaze directions of the respective subject's eyes while the light quantity difference adjusting unit increases the light
(Continued)

quantity difference; and a light quantity difference deciding unit that decides a specific light quantity difference at which a change in the gaze directions due to the increase in the light quantity difference occurs, based on the detection result of the gaze direction detecting unit.

16 Claims, 14 Drawing Sheets

(51) Int. Cl.
*A61B 3/08* (2006.01)
*A61B 3/00* (2006.01)

(56) References Cited

U.S. PATENT DOCUMENTS

| | | | | |
|---|---|---|---|---|
| 5,739,797 | A * | 4/1998 | Karasawa | G02B 27/017 345/8 |
| 5,739,893 | A * | 4/1998 | Karasawa | G02B 27/0176 351/158 |
| 5,764,340 | A * | 6/1998 | Hofeldt | A61B 3/032 351/201 |
| 7,033,025 | B2 * | 4/2006 | Winterbotham | A61H 5/00 351/203 |
| 7,290,878 | B1 * | 11/2007 | Hofeldt | A61B 3/08 351/200 |
| 7,312,765 | B2 * | 12/2007 | de Wit | G09G 3/001 345/611 |
| 8,791,964 | B2 * | 7/2014 | Park | G09G 5/10 345/690 |
| 8,931,905 | B2 * | 1/2015 | Lewis | A61B 5/163 351/246 |
| 9,844,317 | B2 * | 12/2017 | Green | A61B 3/005 |
| 9,867,537 | B2 * | 1/2018 | Bailey | A61B 3/103 |
| 9,905,168 | B1 * | 2/2018 | Richards | G09G 3/3406 |
| 10,251,546 | B2 * | 4/2019 | Foss | A61B 3/08 |
| 10,441,165 | B2 * | 10/2019 | Oz | A61B 3/0091 |
| 10,459,254 | B2 * | 10/2019 | Antaki | H04N 5/2258 |
| 10,516,879 | B2 * | 12/2019 | Eash | H04N 13/337 |
| 2006/0087618 | A1 * | 4/2006 | Smart | A61H 5/005 351/222 |
| 2007/0046776 | A1 * | 3/2007 | Yamaguchi | H04N 13/194 348/53 |
| 2012/0086788 | A1 * | 4/2012 | Wada | G02B 27/0172 348/56 |
| 2012/0105609 | A1 | 5/2012 | Qi | |
| 2012/0307203 | A1 * | 12/2012 | Vendel | G06T 1/00 351/201 |
| 2013/0044291 | A1 | 2/2013 | Kato et al. | |
| 2013/0100400 | A1 * | 4/2013 | Hofeldt | A61B 3/022 351/201 |
| 2013/0120370 | A1 | 5/2013 | Okamoto et al. | |
| 2014/0267636 | A1 * | 9/2014 | Takagi | G02B 27/0172 348/53 |
| 2016/0270656 | A1 * | 9/2016 | Samec | A61B 3/12 |
| 2017/0212587 | A1 * | 7/2017 | Noda | G06F 3/03547 |
| 2018/0203232 | A1 * | 7/2018 | Bouchier | G02C 7/02 |
| 2018/0296085 | A1 * | 10/2018 | Takii | A61B 3/032 |

FOREIGN PATENT DOCUMENTS

| | | |
|---|---|---|
| JP | 2004298289 A | 10/2004 |
| JP | 2006305325 A | 11/2006 |
| JP | 2009178502 A | 8/2009 |
| JP | 2010-099335 A | 5/2010 |
| JP | 2012-095694 A | 5/2012 |
| JP | 2013-102952 A | 5/2013 |
| JP | 2014-124308 A | 7/2014 |

OTHER PUBLICATIONS

Notice of Reasons for Refusal dated Jan. 14, 2020, issued in corresponding Japanese Patent Application No. 2016-055553, 8 pages (with English translation).
Extended Search Report issued in European Application 17766232.7-1124 dated Mar. 15, 2019.
International Preliminary Report on Patentability issued in International Application No. PCT/JP2017/006177 dated Sep. 18, 2018.
English Translation of the Written Opinion of the International Searching Authority issued in International Application No. PCT/JP2017/006177 dated May 16, 2017.

* cited by examiner

EYE-FATIGUE EXAMINING DEVICE AND EYE-FATIGUE EXAMINING METHOD

TECHNICAL FIELD

The present invention relates to an eye-fatigue examining device and an eye-fatigue examining method for objectively examining eye fatigue of a subject's eye.

BACKGROUND ART

In recent years, visual display terminals (VDTs), such as personal computers, tablet terminals, and smart phones, have been globally spread. Long time or long term VDT work using the VDT terminal causes computer vision syndrome (CVS) consisting of indefinite complaint due to overuse of eyes. Diagnosis and treatment of the CVS are performed based on subjective symptoms of a patient due to, for example, a result of a questionnaire made to the patient or the like, so that there is a problem that it is difficult to confirm the diagnosis and treatment. There is also a risk that the CVS may progress of CVS covertly without subjective symptoms in a patient. For this reason, objective examination (evaluation) of CVS useful for diagnosis and treatment of CVS is required.

Here, since symptoms of CVS account for the largest proportion of eye fatigue, objective examination of eye fatigue is required for objective examination of CVS.

For example, Patent Literature 1 describes an eye accommodation function measuring device which arranges a visual target at the furthest far point position where a subject's eye can be clearly viewed based on the result of measuring refractive power of the subject's eye by causing the subject's eye to visually observe the specific visual target, and measures an accommodating function state of the subject's eye visually observing the visual target. In the eye accommodation function measuring device of Patent Literature 1, appearance frequency of a predetermined high-frequency component is calculated by frequency analysis of time variation (accommodating tremor) of refractive power as an index indicating the accommodating function state of the subject's eye. Since there is a close relationship between the accommodating function state and eye fatigue of the subject's eye, eye fatigue of the subject's eye can be objectively examined using the eye accommodation function measuring device of Patent Literature 1.

CITATION LIST

Patent Literature

{PTL 1} Japanese Patent Application Laid-Open No. 2003-70740

SUMMARY OF INVENTION

Technical Problem

When examining eye fatigue of the subject's eye using the eye accommodation function measuring device of the above-mentioned Patent Literature 1, it is necessary to measure time variation of refractive power of the subject's eye. However, in middle-aged and elderly people, function of accommodating response of the eye, that is, accommodating function of a focus position is deteriorated due to a presbyopia eye (presbyopia) which occurs with aging. For this reason, as for middle-aged and elderly people after an initial presbyopia eye, time variation of the refractive power may not be able to measure, and in this case, the eye accommodation function measuring device of the above-mentioned Patent Literature 1 cannot examine eye fatigue of the subject's eye. As a result, there is a problem that it is impossible to examine the eye fatigue of middle-aged and elderly people who are the most populous generation in the aging society, and middle-aged and elderly people cannot receive appropriate diagnosis and treatment.

The present invention has been made in view of the above circumstances, and aims to provide an eye-fatigue examining device and an eye-fatigue examining method which can examine eye fatigue of the subject's eye regardless of the age of a patient.

Solution to Problem

An eye-fatigue examining device for achieving the object of the present invention includes: a light quantity difference adjusting unit configured to increase a light quantity difference between lights respectively incident on right and left subject's eyes; a gaze direction detecting unit configured to detect gaze directions of the respective subject's eyes while the light quantity difference adjusting unit increases the light quantity difference; and a light quantity difference deciding unit configured to decide a specific light quantity difference at which a change in the gaze directions due to an increase in the light quantity difference occurs, based on a detection result of the gaze direction detecting unit. The term "eye fatigue" as used in the present specification includes so-called "eyestrain."

According to this eye-fatigue examining device, because eye fatigue of the subject's eyes can be objectively examined (evaluated) based on fusional faculty of a patient, eye fatigue of the subject's eyes is examined regardless of the age of a patient. Therefore, it is possible to examine eye fatigue of the middle-aged and elderly age group for which anything has not been done conventionally. As a result, objective examinations useful for diagnosis and treatment of CVS become possible.

The eye-fatigue examining device according to another aspect of the present invention includes an outputting unit configured to output the specific light quantity difference decided by the light quantity difference deciding unit as an index of eye fatigue of the subject's eyes. As a result, a doctor can diagnose and evaluate eye fatigue of the subject's eyes.

The eye-fatigue examining device according to another aspect of the present invention includes a visual target displaying unit configured to display an examination visual target to be visually observed by the subject's eyes, and the light quantity difference deciding unit decides the specific light quantity difference, by determining presence or absence of a change in the gaze directions from a state in which the subject's eyes visually observe the examination visual target based on the detection result of the gaze direction detecting unit. This makes it possible to decide the light quantity difference at the time point when destruction of a fusion image due to an increase in a transmittance difference occurs, as the specific light quantity difference.

In the eye-fatigue examining device according to another aspect of the present invention, the gaze direction detecting unit detects positions of Purkinje images of the subject's eyes or positions of pupils of the subject's eyes, and the light quantity difference deciding unit decides the specific light quantity difference, by determining presence or absence of a change in the positions of the Purkinje images or the pupils from a state in which the subject's eyes visually observe the examination visual target. This makes it possible to decide the light quantity difference at the time point when destruction of the fusion image due to the increase in the transmittance difference occurs, as the specific light quantity difference.

In the eye-fatigue examining device according to another aspect of the present invention, the light quantity difference adjusting unit increases the light quantity difference, by decreasing a light quantity of a light incident on one of the subject's eyes and maintaining a light quantity of a light incident on the other of the subject's eyes constant. This makes it possible to cause a change in the gaze directions due to the destruction of the fusion image. Therefore, strength of the fusional faculty of the subject's eye can be evaluated.

In the eye-fatigue examining device according to another aspect of the present invention, the light quantity difference adjusting unit has a transmitting area which can adjust a transmittance of the light incident on at least one of the subject's eyes, and increases the light quantity difference by adjusting the transmittance of the transmitting area. This causes a change in the gaze directions due to the destruction of the fusion image. Therefore, the strength of the fusional faculty of the subject's eye can be evaluated.

In the eye-fatigue examining device according to another aspect of the present invention, when the light quantity difference adjusting unit has the transmitting area on an optical path of the light incident on each of the subject's eyes, the specific light quantity difference decided by the light quantity difference deciding unit is expressed as a difference in the transmittance between the two transmitting areas. This makes it possible to evaluate the strength of the fusional faculty of the subject's eye, based on the difference in the transmittance of the two transmitting areas.

In the eye-fatigue examining device according to another aspect of the present invention, the light quantity difference adjusting unit continuously or stepwise increases the light quantity difference. This makes it possible to cause a change in the gaze direction due to the destruction of the fusion image.

In the eye-fatigue examining device according to another aspect of the present invention, the lights incident on the subject's eyes include a light in a first wavelength band and a light in a second wavelength band different from the first wavelength band, a dichroic mirror is provided on optical paths of the lights reflected by the subject's eyes, the dichroic mirror configured to transmit the light in the first wavelength band and reflect the light in the second wavelength band reflected by the subject's eyes to a side of the optical paths, and the gaze direction detecting unit detects the gaze directions based on a result of detecting the light in the second wavelength band reflected by the dichroic mirror. This makes it possible to objectively examine eye fatigue of the subject's eyes of the patient with both eyes open.

An eye-fatigue examining method for achieving the object of the present invention includes: a light quantity difference adjusting step of increasing a light quantity difference between lights respectively incident on right and left subject's eyes; a gaze direction detecting step of detecting gaze directions of the respective subject's eyes while the light quantity difference is increased in the light quantity difference adjusting step; and a light quantity difference deciding step of deciding a specific light quantity difference at which a change in the gaze directions due to an increase in the light quantity difference occurs, based on a detection result of the gaze direction detecting step.

The eye-fatigue examining method according to another aspect of the present invention includes an outputting step of outputting the specific light quantity difference decided in the light quantity difference deciding step as an index of eye fatigue of the subject's eyes.

The eye-fatigue examining method according to another aspect of the present invention includes a visual target displaying step of displaying an examination visual target to be visually observed by the subject's eyes, and in the light quantity difference deciding step, the specific light quantity difference is decided, by determining presence or absence of a change in the gaze directions from a state in which the subject's eyes visually observe the examination visual target based on the detection result in the gaze direction detecting step.

In the eye-fatigue examining method according to another aspect of the present invention, in the gaze direction detecting step, positions of Purkinje images of the subject's eyes or positions of pupils of the subject's eyes are detected, and in the light quantity difference deciding step, the specific light quantity difference is decided by determining presence or absence of a change of the positions of the Purkinje images or the pupils from a state in which the subject's eyes visually observe the examination visual target.

In the eye-fatigue examining method according to another aspect of the present invention, in the light quantity difference adjusting step, the light quantity difference is increased, by decreasing a light quantity of a light incident on one of the subject's eyes and maintaining a light quantity of a light incident on the other of the subject's eyes constant.

The eye-fatigue examining method according to another aspect of the present invention includes arranging a transmitting area which can adjust a transmittance of a light, on an optical path of the light incident on at least one of the subject's eyes, and in the light quantity difference adjusting step, the light quantity difference is increased by adjusting the transmittance of the transmitting area.

In the eye-fatigue examining method according to another aspect of the present invention, when the transmitting area is arranged on an optical path of the light incident on each of the subject's eyes, the specific light quantity difference decided in the light quantity difference deciding step is expressed as a difference in the transmittance between the two transmitting areas.

In the eye-fatigue examining method according to another aspect of the present invention, in the light quantity difference adjusting step, the light quantity difference is continuously or stepwise increased.

In the eye-fatigue examining method according to another aspect of the present invention, the lights incident on the subject's eyes include a light in a first wavelength band and a light in a second wavelength band different from the first wavelength band, a dichroic mirror is arranged on optical paths of the lights reflected by the subject's eyes, the dichroic mirror configured to transmit the light in the first wavelength band and reflect the light in the second wavelength band reflected by the subject's eyes to a side of the optical paths, and in the gaze direction detecting step, the gaze directions are detected based on a result of detecting the light in the second wavelength band reflected by the dichroic mirror.

Advantageous Effects of Invention

According to the eye-fatigue examining device and the eye-fatigue examining method of the present invention, eye fatigue of the subject's eye can be examined regardless of the age of a patient.

DESCRIPTION OF EMBODIMENTS

Overall Configuration of Eye-Fatigue Examining Device

Figure 1:
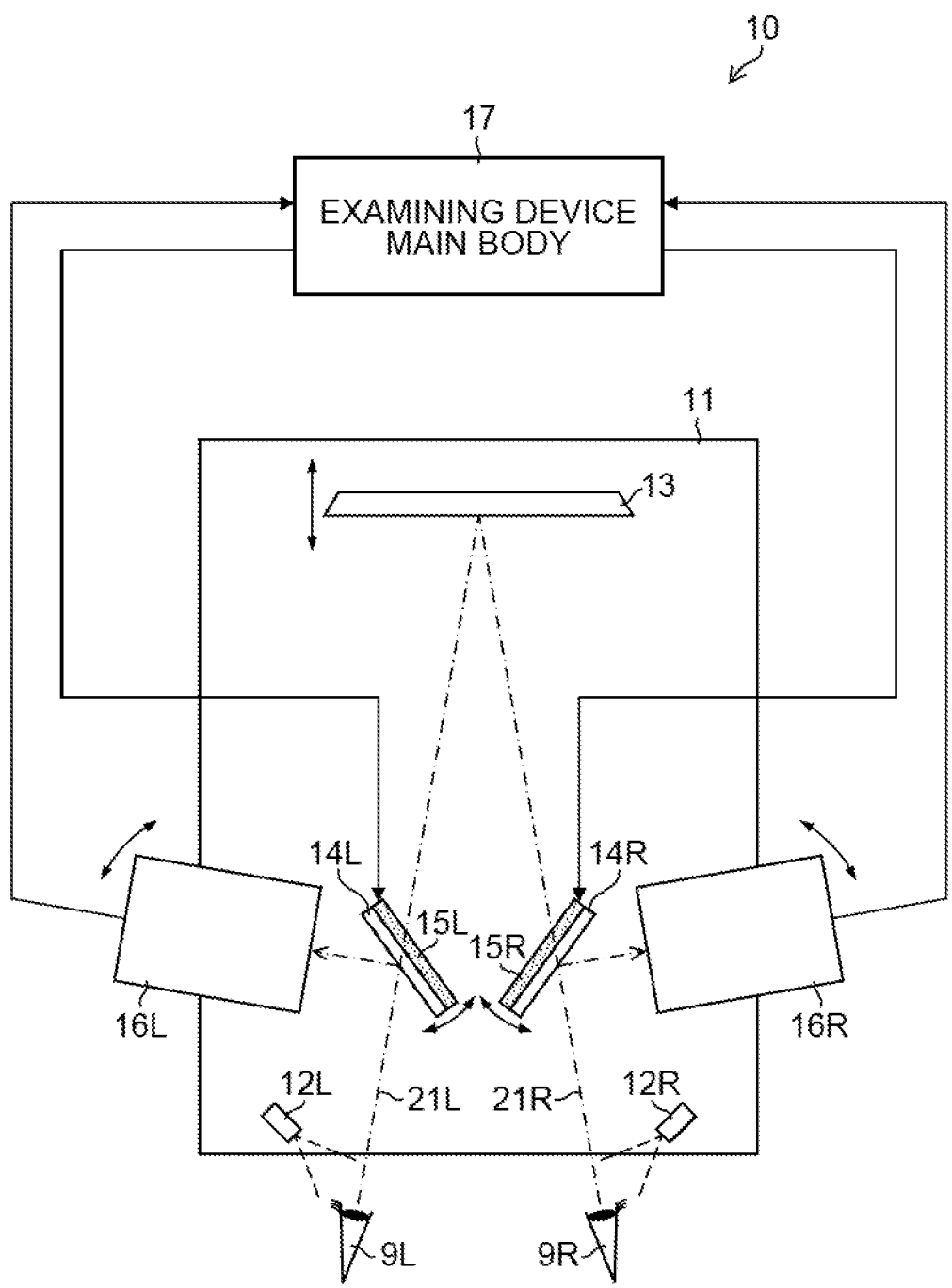
FIG. 1 is a schematic top view of an eye-fatigue examining device for objectively examining eye fatigue of right and left subject's eyes of a patient based on strength of a fusion image of a patient.

FIG. 1 is a schematic top view of an eye-fatigue examining device 10 objectively examining eye fatigue of right and left subject's eyes 9R, 9L of a patient based on strength (fusional faculty) of a fusion image of the patient. Here, the "fusion image" is a function of fusing retinal images of both eyes and recognizing them as one image. To prevent complication of the drawing, illustration of parts other than the subject's eyes 9R, 9L of the patient is omitted.

As illustrated in FIG. 1, the eye-fatigue examining device 10 includes an optometric table 11, a pair of infrared light sources 12R, 12L, a visual target displaying unit 13, a pair of dichroic mirrors 14R, 14L, a pair of liquid crystal shutters 15R, 15L, a pair of measuring units 16R, 16L, and an examining device main body 17.

On the optometric table 11, each part of the eye-fatigue examining device 10 except the examining device main body 17 is arranged. Also, a face receiving part, which is not shown, is arranged at the front-end part (the lower end part in the drawing) positioned on a patient side of the optometric table 11. The patient places his/her chin on this face receiving part and puts the forehead, whereby positions of the subject's eyes 9R, 9L on the optometric table 11 are fixed.

Infrared light sources 12R, 12L are attached to the above-described face receiving part (not shown). The infrared light source 12R is attached near the subject's eye 9R, and irradiates the subject's eye 9R with near infrared light. In addition, the infrared light source 12L is attached near the subject's eye 9L, and irradiates the subject's eye 9L with near infrared light. A wavelength band of the near infrared light irradiated by the infrared light sources 12R, 12L is, for example, 950 nm.

The visual target displaying unit 13 is arranged at a rear-end part opposite to a front-end part of the optometric table 11 so as to be positioned in a front direction of the subject's eyes 9R, 9L. The visual target displaying unit 13 can be moved and adjusted in the front-rear direction in which the visual target displaying unit 13 approaches the subject's eyes 9R, 9L or separates from the subject's eyes 9R, 9L by a slide mechanism, which is not shown. As a result, the visual target displaying unit 13 can be moved to a distance (for example, 30 cm, 50 cm, 1 m) at which the subject's eyes 9R, 9L can easy visually recognize the visual target displaying unit 13 according to refractive powers of the subject's eyes 9R, 9L.

Figure 2:
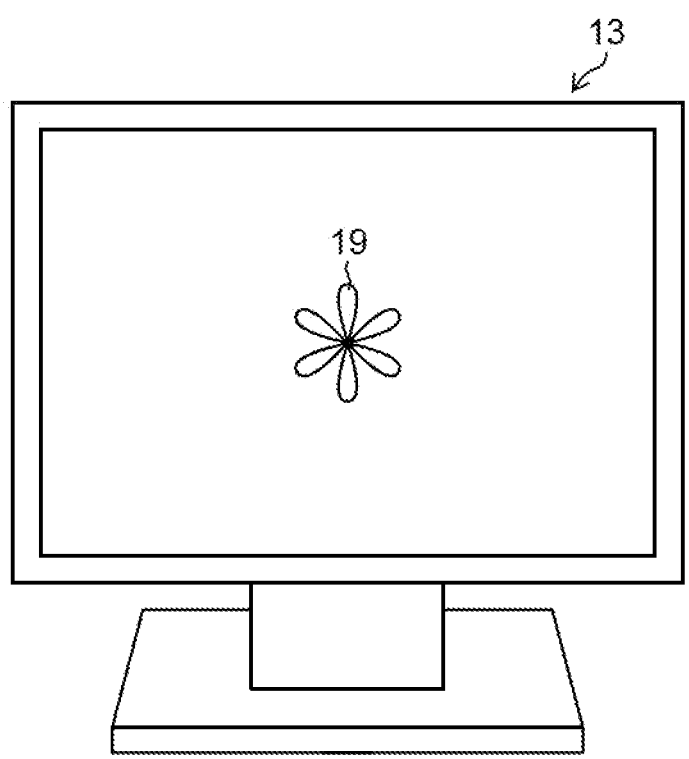
FIG. 2 is a front view of a visual target displaying unit as viewed from a side of the subject's eye.

FIG. 2 is a front view of the visual target displaying unit 13 as viewed from a side of the subject's eyes 9R, 9L. During examination of the eye fatigue, the visual target displaying unit 13 displays an examination visual target 19 to be visually observed by the subject's eyes 9R, 9L. As a displaying method of the examination visual target 19 by the visual target displaying unit 13, various methods such as a method of displaying an image of the examination visual target 19 on a liquid crystal monitor or the like, or a method of sticking a sheet on which an image of the examination visual target 19 is printed can be adopted.

Returning to FIG. 1, the dichroic mirror 14R is arranged on an optical path 21R (on a visual line of the subject's eye 9R) connecting the examination visual target 19 and the subject's eye 9R. On the other hand, the dichroic mirror 14L is arranged on an optical path 21L (on a visual line of the subject's eye 9L) connecting the examination visual target 19 and the subject's eye 9L. The dichroic mirrors 14R, 14L are rotatably adjusted around an axis perpendicular to an upper surface of the optometric table 11. The dichroic mirror 14R is arranged on the optical path 21R in a state inclined by 45 degrees with respect to the optical path 21R, and the dichroic mirror 14L is arranged on the optical path 21L in a state inclined by 45 degrees with respect to the optical path 21L.

The dichroic mirrors 14R, 14L transmit visible light (wavelength band: about 380 nm to 780 nm) corresponding to the light in the first wavelength band of the present invention therethrough and reflect light in other wavelength bands, for example, near infrared light (wavelength band: about 800 nm to 2500 nm) corresponding to the light in the second wavelength band of the present invention. As a result, the examination visual target 19 can be visually observed (natural vision) by the subject's eyes 9R, 9L.

On the other hand, the near infrared light traveling along the optical path 21R among the near infrared light reflected by the subject's eye 9R is reflected toward a right side of the optical path 21R by the dichroic mirror 14R. The near infrared light traveling along the optical path 21L among the near infrared light reflected by the subject's eye 9L is reflected toward a left side of the optical path 21L by the dichroic mirror 14L.

Figure 3:
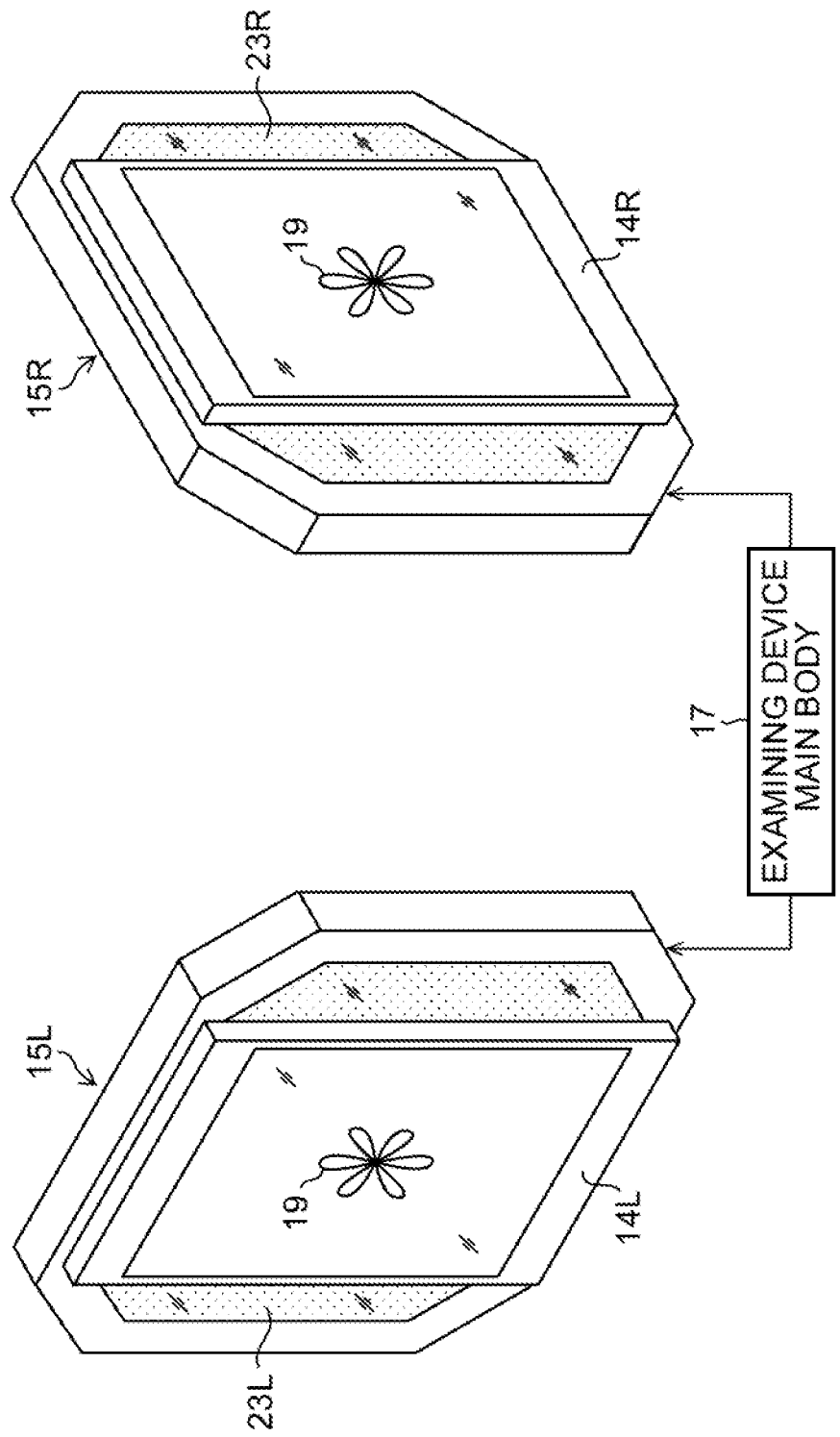
FIG. 3 is a front view of a liquid crystal shutter as viewed from a side of the patient.

FIG. 3 is a front view of the liquid crystal shutters 15R, 15L as viewed from the patient side. As illustrated in FIG. 3, the liquid crystal shutters 15R, 15L function as a part of the light quantity difference adjusting unit of the present invention. The liquid crystal shutter 15R is attached on a surface of the dichroic mirror 14R on a side of the visual target displaying unit 13 and the liquid crystal shutter 15L is attached on a surface of the dichroic mirror 14L on the side of the visual target displaying unit 13. As a result, the liquid crystal shutters 15R, 15L are arranged on the optical paths 21R, 21L, respectively. Accordingly, the subject's eye 9R visually observes the examination visual target 19 through the dichroic mirror 14R and the liquid crystal shutter 15R, and the subject's eye 9L visually observes the examination visual target 19 through the dichroic mirror 14L and the liquid crystal shutter 15L.

Positions of the liquid crystal shutters 15R, 15L are not particularly limited as long as they are arranged on the optical paths 21R, 21L, respectively. However, from the viewpoint of preventing the near infrared lights reflected by the subject's eyes 9R, 9L from being attenuated by the liquid crystal shutters 15R, 15L, it is preferable that the liquid crystal shutters 15R, 15L are arranged between the dichroic mirrors 14R, 14L and the visual target displaying unit 13.

The liquid crystal shutters 15R, 15L have transmitting areas 23R, 23L (see FIG. 3) through which the lights traveling along the optical paths 21R, 21L (visible light) pass, respectively. The liquid crystal shutters 15R, 15L can arbitrarily adjust a transmittance of lights passing through the transmitting areas 23R, 23L by arbitrarily changing a density of the transmitting areas 23R, 23L, respectively. Thereby, it is possible to individually adjust a brightness of the examination visual target 19 visually observed by the subject's eyes 9R, 9L. A transmittance of each of the transmitting areas 23R, 23L is adjusted by the examining device main body 17 to be described later.

In the present embodiment, X-FOS (G 2)-CE (manufactured by LC-Tec Holding AB) is used as the liquid crystal shutters 15R, 15L. In this case, the actual measured liquid crystal transmittance of the liquid crystal shutters 15R, 15L is 23.0% at the maximum and 0.07% at the minimum when measured with a spectroradiometer SR-LEDW manufactured by TOPCON CORPORATION, for example. Further, the delay time (response time) of the liquid crystal shutters 15R, 15L is 2.5 ms or less.

Returning to FIG. 1, the measuring unit 16R is arranged on a right side of the dichroic mirror 14R, and the measuring unit 16L is arranged on a left side of the dichroic mirror 14L. The measuring units 16R, 16L can be rotationally adjusted around an axis perpendicular to the upper surface of the optometric table 11.

The measuring units 16R, 16L emit near infrared lights (wavelength of 840 nm) having wavelength bands different from the above-mentioned infrared light sources 12R, 12L toward the dichroic mirrors 14R, 14L, respectively. The near infrared lights having a wavelength of 840 nm are respectively reflected by the dichroic mirrors 14R, 14L toward the subject's eyes 9R and 9L. As a result, the near infrared lights of two wavelengths (wavelengths of 950 nm and 840 nm) enter the subject's eyes 9R, 9L. Then, the near infrared lights of two wavelengths, respectively having been reflected by the subject's eyes 9R, 9L, enter the dichroic mirrors 14R, 14L through the optical paths 21R, 21L, and are reflected toward the measuring units 16R, 16L by the dichroic mirrors 14R, 14L, respectively.

The measuring units 16R, 16L constitute a part of the gaze direction detecting unit of the present invention. Each of the measuring units 16R, 16L receives the near infrared lights of two wavelengths reflected by the dichroic mirrors 14R, 14L, and outputs light receiving signals for each wavelength band to the examining device main body 17. Each of the measuring units 16R, 16L includes: an anterior eye segment observing system 25 which receives the near infrared lights having a wavelength of 950 nm and outputs a light receiving signal used for detecting the gaze direction; and an aberration measuring system 26 which receives the near infrared lights having a wavelength of 840 nm and outputs a light receiving signal used for detecting the focus positions (wavefront aberration) of the subject's eyes 9R, 9L (see FIG. 4).

As described above, in the present embodiment, the near infrared lights of two wavelengths reflected by the dichroic mirrors 14R, 14L are used as measuring lights for detecting the gaze directions and focus positions of the subject's eyes 9R, 9L. As a result, it is possible to detect the gaze directions and the focus positions of the subject's eyes 9R, 9L while the examination visual target 19 is visually observed (natural vision) with the subject's eyes 9R, 9L.

Configuration of Measuring Unit

Figure 4:
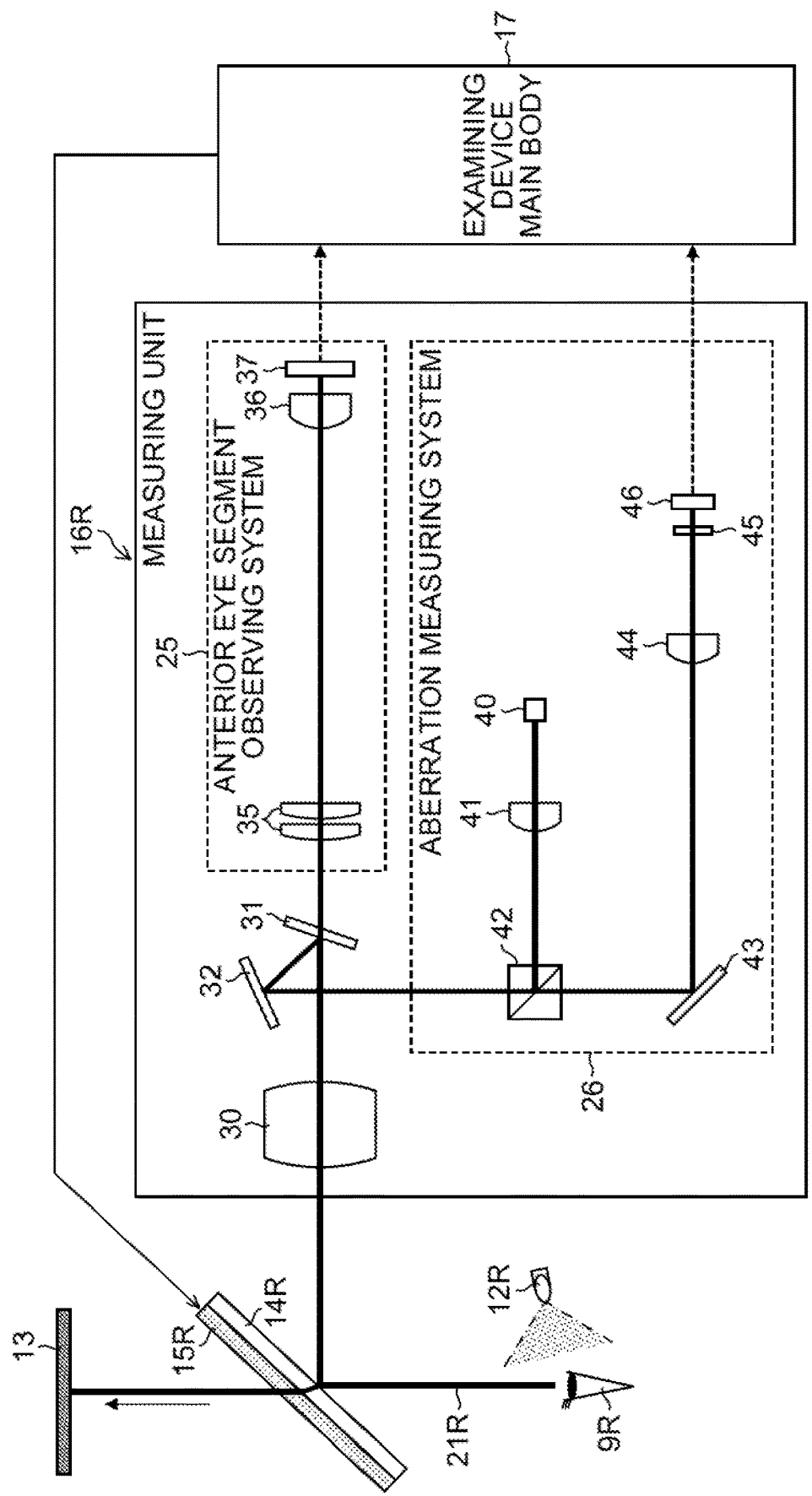
FIG. 4 is a block diagram illustrating a configuration of a measuring unit.

FIG. 4 is a block diagram illustrating a configuration of the measuring unit 16R. As illustrated in FIG. 4, the measuring unit 16R includes an objective lens 30, a dichroic mirror 31, and a mirror 32, in addition to the above-mentioned anterior eye segment observing system 25 and the aberration measuring system 26.

The objective lens 30 emits the near infrared light having a wavelength of 840 nm incident through the aberration measuring system 26, which will be described later, the mirror 32, and the dichroic mirror 31 toward the dichroic mirror 14R. In addition, the near infrared lights of two wavelengths (wavelength of 840 nm, wavelength of 950 nm) enter the objective lens 30 from the subject's eye 9R through the optical path 21R and the dichroic mirror 14R. Then, the objective lens 30 emits the near infrared light of two wavelengths incident from the dichroic mirror 14R toward the dichroic mirror 31.

The dichroic mirror 31 transmits the near infrared light having a wavelength of 950 nm and reflects the near infrared light having a wavelength of 840 nm. As a result, the dichroic mirror 31 reflects the near infrared light having a wavelength of 840 nm incident from the aberration measuring system 26 through the mirror 32 toward the objective lens 30. Further, the dichroic mirror 31 transmits the near infrared light having a wavelength of 950 nm of the near infrared lights of two wavelengths which have been incident from the objective lens 30, to make it incident on the anterior eye segment observing system 25, and reflects the near infrared light having a wavelength of 840 nm toward the mirror 32.

The mirror 32 reflects the near infrared light having a wavelength of 840 nm incident from one of the aberration measuring system 26 and the dichroic mirror 31 toward the other.

The anterior eye segment observing system 25 includes a relay lens 35, an imaging lens 36, and a CCD (Charge-Coupled Device) type or a CMOS (Complementary Metal Oxide Semiconductor) type imaging device 37. The relay lens 35 emits the near infrared light having a wavelength of 950 nm incident from the dichroic mirror 31 toward the imaging lens 36. The imaging lens 36 images the near infrared light having a wavelength of 950 nm incident from the relay lens 35 on a light receiving surface of the imaging device 37.

The imaging device 37 receives (images) the near infrared light having a wavelength of 950 nm imaged by the imaging lens 36, and outputs a light receiving signal indicating an image of the anterior eye segment of the subject's eye 9R to the examining device main body 17.

As the aberration measuring system 26, a binocular wavefront sensor is used. The aberration measuring system 26 includes a semiconductor element 40 such as an SDL (Super luminescent diode), a collimator lens 41, a beam splitter 42, a mirror 43, an imaging lens 44, a Hartmann plate 45, and a CCD type or a CMOS type of an imaging device 46.

The semiconductor element 40 emits the near infrared light having a wavelength of 840 nm toward the collimator lens 41. The collimator lens 41 converts the near infrared light having a wavelength of 840 nm incident from the semiconductor element 40 into parallel light and then emits it toward the beam splitter 42.

The beam splitter 42 reflects the near infrared light having a wavelength of 840 nm incident from the collimator lens 41 toward the mirror 32. Further, the beam splitter 42 transmits the near infrared light having a wavelength of 840 nm incident from the mirror 32 through the dichroic mirror 31 and the like as it is, and makes it incident on the mirror 43.

The mirror 43 reflects the near infrared light having a wavelength of 840 nm incident from the beam splitter 42 toward the imaging lens 44. The imaging lens 44 images the near infrared light having a wavelength of 840 nm incident from the mirror 43 onto the Hartmann plate 45.

On the surface of the Hartmann plate 45, many micro lenses having equal focal lengths are formed. The Hartmann plate 45 divides the near infrared light having a wavelength of 840 nm incident from the imaging lens 44 into a plurality of luminous fluxes corresponding to each micro lens and images each luminous flux on the light receiving surface of the imaging device 46.

The imaging device 46 receives (images) the plurality of luminous fluxes imaged on the light receiving surface by the Hartmann plate 45, and outputs a light receiving signal indicating a plurality of point images corresponding to respective luminous fluxes to the examining device main body 17.

Since the measuring unit 16L has the same configuration as the measuring unit 16R, explanation and illustration of each part of the measuring unit 16L will be omitted. The measuring unit 16L receives the near infrared light having a wavelength of 950 nm reflected by the subject's eye 9L at the anterior eye segment observing system 25, and outputs a light receiving signal indicating an image of the anterior eye segment of the subject's eye 9L to the examining device main body 17. Further, the measuring unit 16L receives the near infrared light having a wavelength of 840 nm reflected by the subject's eye 9L at the aberration measuring system 26, and outputs a light receiving signal indicating a plurality of point images to the examining device main body 17.

Configuration of Examining Device Main Body

Figure 5:
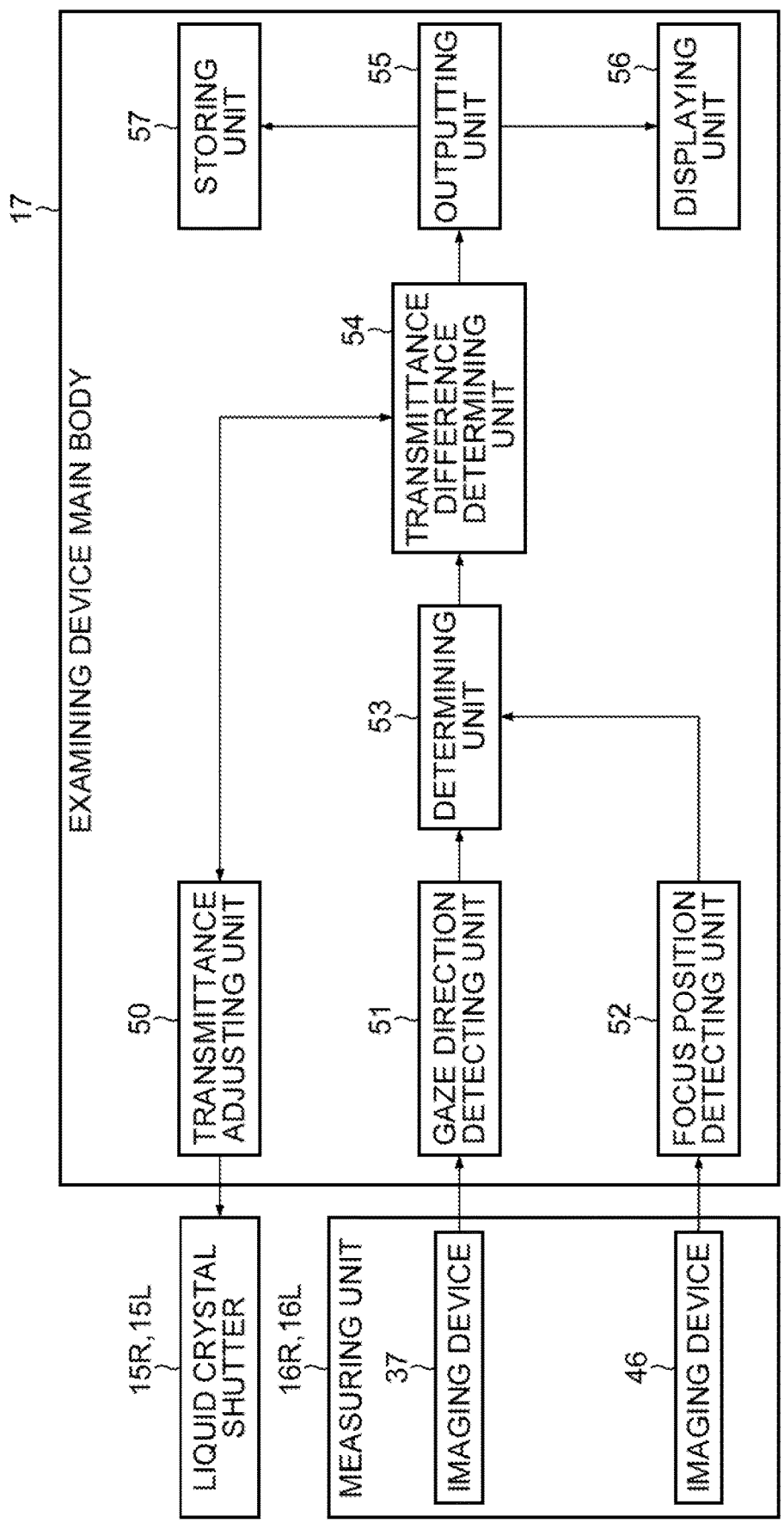
FIG. 5 is a block diagram illustrating a configuration of an examining device main body.

FIG. 5 is a block diagram illustrating a configuration of the examining device main body 17. As the examining device main body 17, various arithmetic processing devices such as a personal computer may be used.

As illustrated in FIG. 5, the examining device main body 17 includes a transmittance adjusting unit 50, a gaze direction detecting unit 51, a focus position detecting unit 52, a determining unit 53, a transmittance difference determining unit 54, an outputting unit 55, a displaying unit 56, and a storing unit 57. The configuration from the transmittance adjusting unit 50 to the outputting unit 55 may be achieved by, for example, a CPU (Central Processing Unit) or FPGA (field-programmable gate array).

The transmittance adjusting unit 50 and the liquid crystal shutters 15R, 15L constitute the light quantity difference adjusting unit of the present invention. The transmittance adjusting unit 50 adjusts the transmittance (density) of the transmitting areas 23R, 23L of the liquid crystal shutters 15R, 15L.

Figure 6:
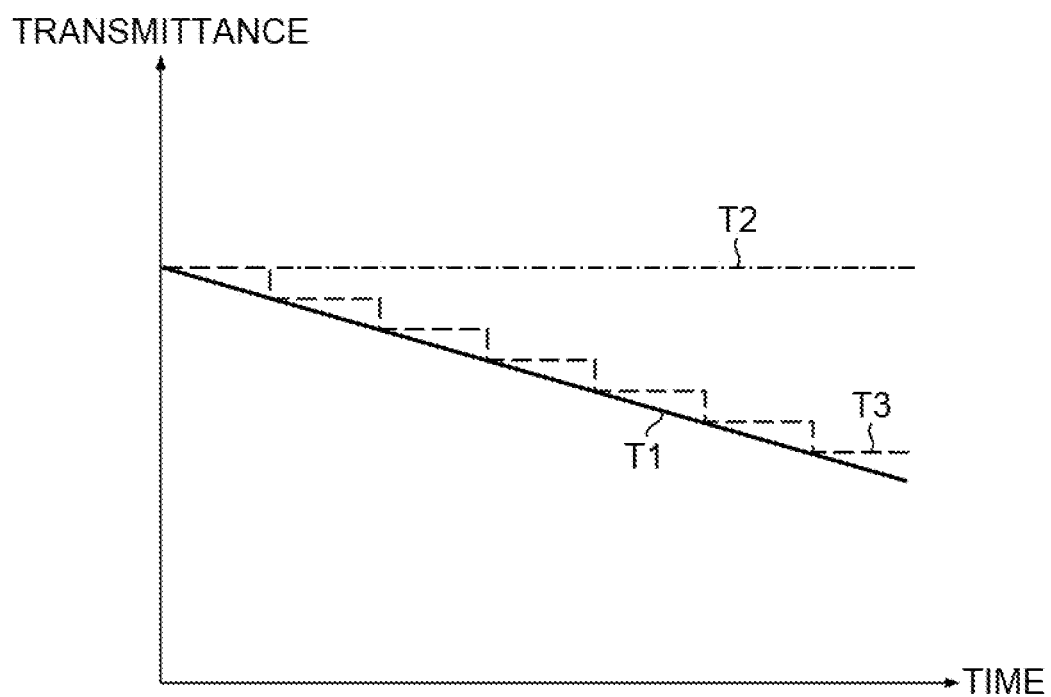
FIG. 6 is an explanatory diagram for explaining adjustment of transmittance of a transmitting area of the liquid crystal shutter.

FIG. 6 is an explanatory diagram for explaining adjustment of transmittance of the transmitting areas 23R, 23L of the liquid crystal shutters 15R, 15L. As illustrated in FIG. 6, when operation for starting examination of the eye fatigue of the subject's eyes 9R, 9L is performed, the transmittance adjusting unit 50 continuously decreases the transmittance corresponding to one of the transmitting areas 23R, 23L as indicated by the straight line T1 with the lapse of time, and maintains the transmittance corresponding to the other of the transmitting areas 23R, 23L constant (for example, maximum transmittance) as indicated by a straight line T2. As a result, the light quantity of visible light incident on one of the subject's eyes 9R, 9L continuously decreases with the lapse of time, and the light quantity of visible light incident on the other of the subject's eyes 9R, 9L is maintained constant. As a result, the transmittance difference, which is the difference in the transmittance between the transmitting areas 23R, 23L, increases with the lapse of time. Therefore, the light quantity difference which is the difference in the light quantity between the visible lights respectively incident on the subject's eyes 9R, 9L, increases.

In the present embodiment, the light quantity of visible light incident on the non-dominant eye on a side opposite to the dominant eye of the patient among the subject's eyes 9R, 9L is continuously decreased with the lapse of time.

Further, in the present embodiment, the transmittance corresponding to one of the transmitting areas 23R, 23L is continuously decreased with the lapse of time, but may be decreased stepwise as indicated by the broken line T3. As a result, the light quantity of the visible light incident on one of the subject's eyes 9R, 9L decreases stepwise with the lapse of time.

The gaze direction detecting unit 51 and the measuring units 16R, 16L constitute the gaze direction detecting unit of the present invention. While the transmittance adjusting unit 50 increases the transmittance difference (light quantity difference) between the transmitting areas 23R, 23L, the gaze direction detecting unit 51 detects the gaze directions of the subject's eyes 9R, 9L, based on light receiving signals input from the imaging devices 37 of both of the measuring units 16R, 16L.

Figure 7:
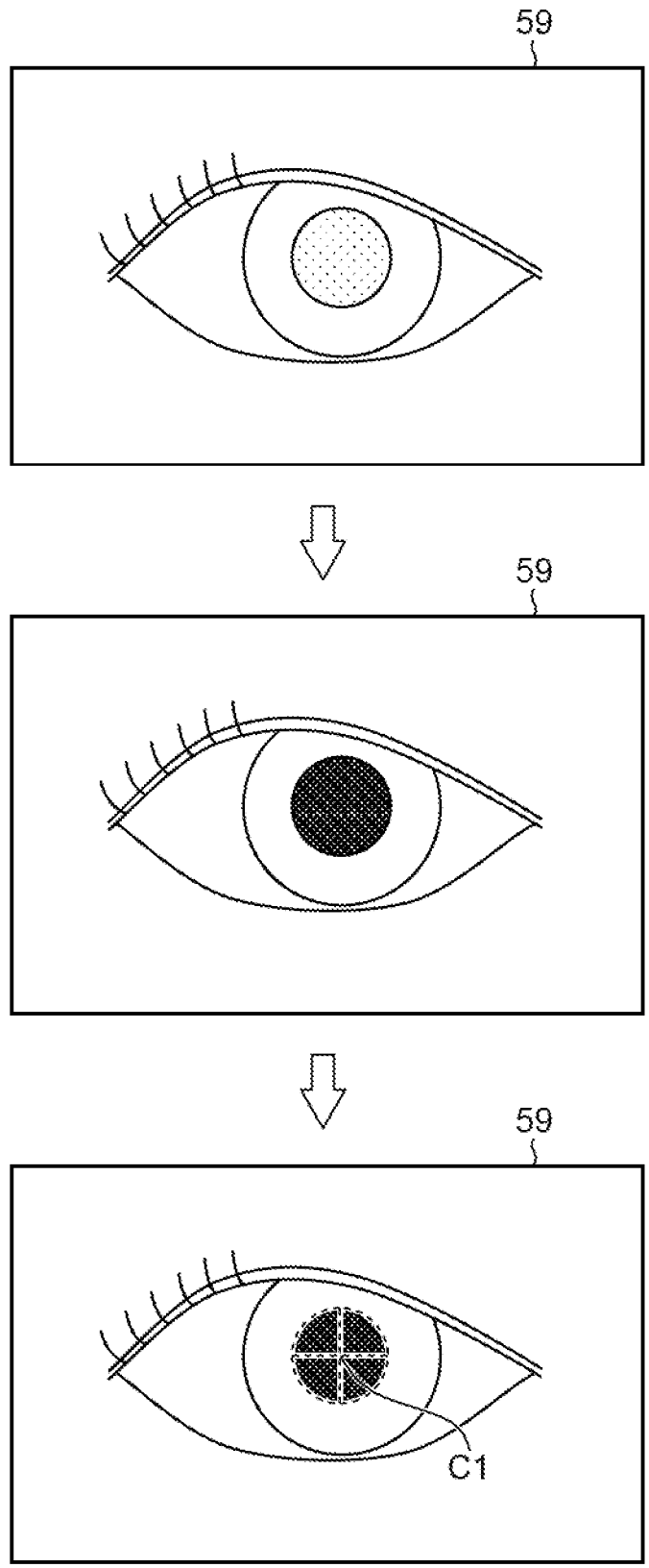
FIG. 7 is an explanatory diagram for explaining an example of gaze direction detection using an image measuring method (dark pupil method).

FIG. 7 is an explanatory diagram for explaining an example of gaze direction detection using the image measuring method (dark pupil method). As illustrated in the upper part of FIG. 7, the gaze direction detecting unit 51 generates anterior eye segment images 59 (only one anterior eye segment image 59 of the subject's eye 9R is illustrated in the drawing) indicating the anterior eye segments of the subject's eyes 9R, 9L, based on the light receiving signals input from both the imaging devices 37 of both the measuring units 16R, 16L.

Next, as illustrated in the middle stage of FIG. 7, the gaze direction detecting unit 51 binarizes the anterior eye segment images 59 of the subject's eyes 9R, 9L with a predetermined luminance threshold value. Since the pupils of the subject's eyes 9R, 9L have lower luminance than the surrounding areas, when the anterior eye segment images 59 are binarized, the areas corresponding to the pupils in the anterior eye segment images 59 become black pixel areas, and the surrounding areas of the pupils become white pixel areas. Thus, the pupil areas of the subject's eyes 9R, 9L can be specified from the anterior eye segment images 59.

As illustrated in the lower part of FIG. 7, the gaze direction detecting unit 51 obtains the center coordinates C1 of the pupil areas (black pixel area) of the subject's eyes 9R, 9L from the binarized anterior eye segment images 59, and detects the gaze directions of the subject's eyes 9R, 9L, based on the obtained center coordinates C1 and the known geometrical structure of the eyeball. Since detection of the gaze direction by the dark pupil method is a well-known technique, the detailed description thereof will be omitted.

In addition, when the gaze directions are detected by the image measuring method, in addition to the dark pupil method, for example, positions of spot images (xy spot) imaged on retinas of the subject's eyes 9R, 9L may be detected, or positions of Purkinje images 59p (See FIG. 8) may be detected.

Figure 8:
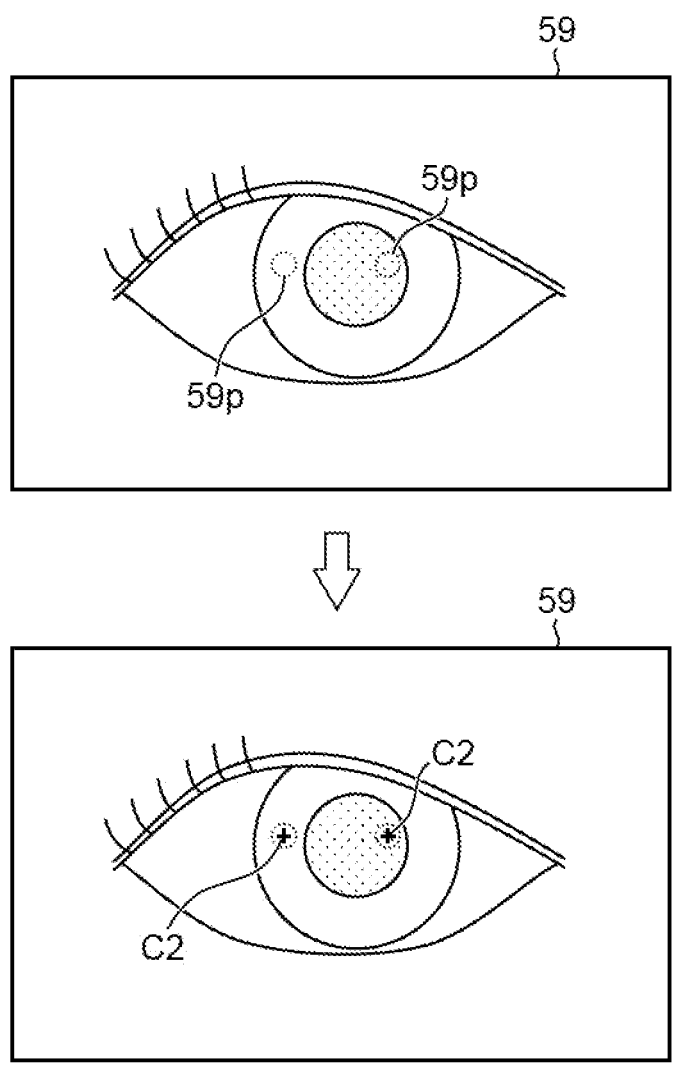
FIG. 8 is an explanatory diagram for explaining an example of gaze direction detection using a Purkinje image.

FIG. 8 is an explanatory diagram for explaining an example of gaze direction detection using a Purkinje image 59p. As illustrated in the upper part of FIG. 8, due to an incidence of near infrared light, the Purkinje image 59p which is a reflection image of the near infrared light, is generated on a corneal surface of each of the subject's eyes 9R, 9L. A position of the Purkinje image 59p varies according to the change of the gaze direction of each subject's eyes 9R, 9L. Therefore, the positions of the Purkinje images 59p are information indicating the gaze directions of the subject's eyes 9R, 9L.

As illustrated in the lower part of FIG. 8, the gaze direction detecting unit 51 analyzes the anterior eye segment images 59 of the subject's eyes 9R, 9L, and detects the position coordinates C2 of the Purkinje images 59p from the anterior eye segment images 59. Then, the gaze direction detecting unit 51 detects the gaze direction of the subject's eyes 9R, 9L, based on the relative positions between the positions of the Purkinje images 59p indicated by the position coordinates C2 and the centers of the pupils. The method of detecting the gaze direction using the Purkinje image 59p is a well-known technique, and the detailed description thereof will be omitted.

As described above, while the transmittance adjusting unit 50 increases the transmittance difference (light quantity difference) between the transmitting areas 23R, 23L, the gaze direction detecting unit 51 continuously performs the detection of the gaze directions of the subject's eyes 9R, 9L, and the outputs the detection result to the determining unit 53.

In this embodiment, the gaze directions of the subject's eyes 9R, 9L is detected using the image measuring method, but the gaze directions of the subject's eyes 9R, 9L may be detected using another method. For example, various methods such as an EOG (electro electro-oculography) method of detecting the gaze direction by measuring a myoelectric signal that varies according to the movement of the muscles around eyeballs of the subject's eyes 9R, 9L, or a search coil method for detecting the gaze direction by mounting contact lenses each incorporating a search coil to the subject's eyes 9R, 9L, may be used.

Returning to FIG. 5, while the transmittance adjusting unit 50 increases the transmittance difference (light quantity difference) between the transmitting areas 23R, 23L, the focus position detecting unit 52 detects the focus positions of the subject's eyes 9R, 9L, based on the light receiving signals input from both the imaging devices 46 of both the measuring units 16R, 16L. For example, the focus position detecting unit 52 performs Zernike analysis or the like based on the light receiving signals input from the imaging devices 46 to measure the wavefront aberrations of the subject's eyes 9R, 9L, and detects the focus positions (adjustment positions) of the subject's eyes 9R, 9L based on the measuring results of the wavefront aberrations. Since the focus position detection method by the wavefront aberration measurement processing is a well-known technique, the detailed description is omitted.

While the transmittance adjusting unit 50 increases the transmittance difference (light quantity difference) between the transmitting areas 23R, 23L, the focus position detecting unit 52 continuously performs detection of the focus positions of the subject's eyes 9R, 9L, and output of the detection result to the determining unit 53.

While the transmittance adjusting unit 50 increases the transmittance difference (light quantity difference) between the transmitting areas 23R, 23L, the determining unit 53 detects a change in the gaze directions of the subject's eyes 9R, 9L due to the increase in the transmittance difference. More specifically, the determining unit 53 detects a change in the gaze directions of the subject's eyes 9R, 9L due to the destruction of the fusion image caused by the increase in the transmittance difference.

Figure 9:
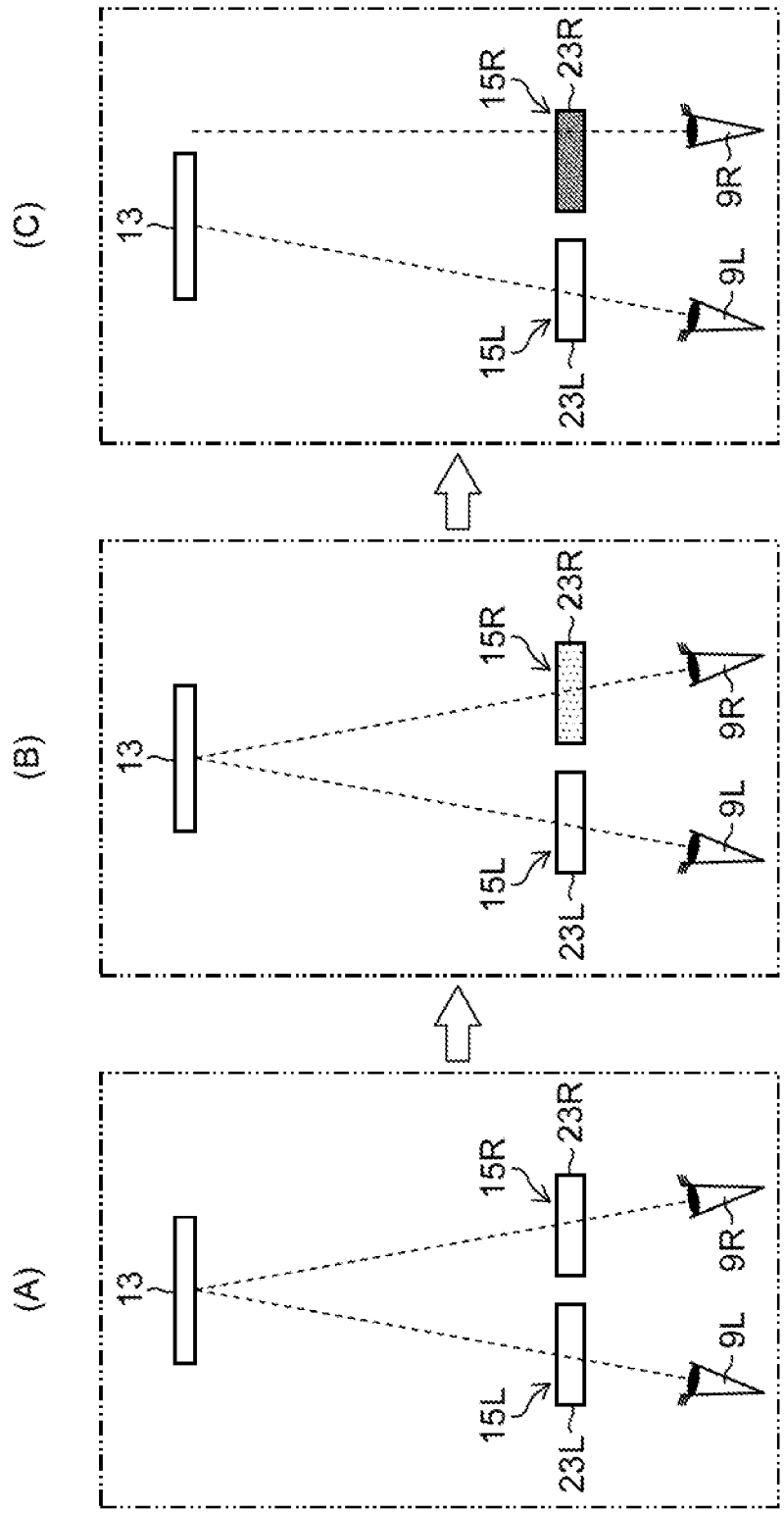
FIG. 9 is an explanatory diagram for explaining a change in a gaze direction of a subject's eye due to destruction of the fusion image caused by an increase in transmittance difference.

FIG. 9, which includes Parts (A), (B) and (C), is an explanatory diagram for explaining a change in the gaze directions of the subject's eyes 9R, 9L due to the destruction of the fusion image caused by the increase in transmittance difference. As illustrated in Part (A) in FIG. 9, when the transmittance difference between the transmitting areas 23R, 23L is zero (including substantially zero), that is, when the light quantity difference between visible lights incident on the subject's eyes 9R, 9L is zero, a fusion image which the patient recognizes the images of the examination visual target 19 visually observed by respective subject's eyes 9R, 9L, as one image is established. Next, as illustrated in Part (B) in FIG. 9, when the transmittance of one of the transmitting areas 23R, 23L (here, the transmitting area 23R) is reduced with the lapse of time to increase the transmittance difference between the transmitting areas 23R, 23L, if the transmittance difference is within a certain range, a fusion image is established.

Then, as illustrated in Part (C) in FIG. 9, when the transmittance difference between the transmitting areas 23R, 23L increases beyond the certain range, the patient can not recognize the image of the examination visual target 19 respectively visually observed with the subject's eyes 9R, 9L as one image and the congestion is not maintained. Therefore, the fusion image is destroyed. As a result, a change occurs in the gaze direction of the subject's eyes 9R. The present inventors have confirmed that there is a correlation between the eye fatigue of the subject's eyes 9R, 9L and the strength of the fusional faculty of the patient, specifically, that the fusional faculty of the patient declines as the eye fatigue increases. Here, the declination of the fusional faculty of the patient means that the magnitude of the transmittance difference (light quantity difference) at which the fusion image is destroyed decreases, that is, the fusion image is destroyed with a low transmittance difference. Therefore, in the present embodiment, the determining unit 53 determines presence or absence of a change in the gaze directions of the subject's eyes 9R, 9L due to the increase in the transmittance difference.

Returning to FIG. 5, while the transmittance difference between the transmitting areas 23R, 23L increases, the determining unit 53 determines presence or absence of a change in the gaze directions from a state in which the subject's eyes 9R, 9L visually observe the examination visual target 19, based on the gaze direction detection results input from the gaze direction detecting unit 51 and the focus position detection results input from the focus position detecting unit 52. Further, the determining unit 53 outputs the determination result to the transmittance difference determining unit 54.

Here, the gaze directions of the subject's eyes 9R, 9L can be detected based on the gaze direction detection results input from the gaze direction detecting unit 51. In addition, it can be determined which position (distance) the subject's eyes 9R, 9L are visually observing, based on the focus position detection results of the subject's eyes 9R, 9L input from the focus position detecting unit 52. Therefore, this determination can be made more reliable by using the focus position detection results of the subject's eyes 9R, 9L for determination of presence or absence (presence or absence of formation of a fusion image) of a change in the gaze directions. Therefore, even in the case of a middle-aged and elderly patient having focus adjustment function degraded, if the focus adjustment function slightly remains, the determination accuracy of the determining unit 53 can be improved.

The transmittance difference determining unit 54 and the determining unit 53 function as the light quantity difference deciding unit of the present invention. When receiving the input of the determination result indicating the presence of the change in the gaze directions (see Part (C) in FIG. 9) from the determining unit 53, the transmittance difference determining unit 54 obtains the transmittances of the transmitting areas 23R, 23L at the time when the change in the gaze directions occurs from the transmittance adjusting unit 50. As to the transmittances of the transmitting areas 23R, 23L, calibrated values may be obtained by conducting transmittance measurement in advance.

Then, the transmittance difference determining unit 54 determines a specific transmittance difference (hereinafter, simply referred to as a specific transmittance difference) at which the change in the gaze directions of the subject's eyes 9R, 9L occurs, based on the obtained transmittances of the transmitting areas 23R, 23L, and outputs transmittance difference information indicating the decided specific transmittance difference to the outputting unit 55. This specific transmittance difference corresponds to the specific light quantity difference of the present invention.

The outputting unit 55 outputs the transmittance difference information input from the transmittance difference determining unit 54 to the displaying unit 56 and the storing unit 57 respectively, as indices indicating eye fatigue of the subject's eyes 9R, 9L.

The displaying unit 56 displays the transmittance difference information input from the outputting unit 55. Further, the storing unit 57 stores the transmittance difference information input from the outputting unit 55 in association with, for example, unique identification information of the patient.

Operation of Eye-Fatigue Examining Device

Figure 10:
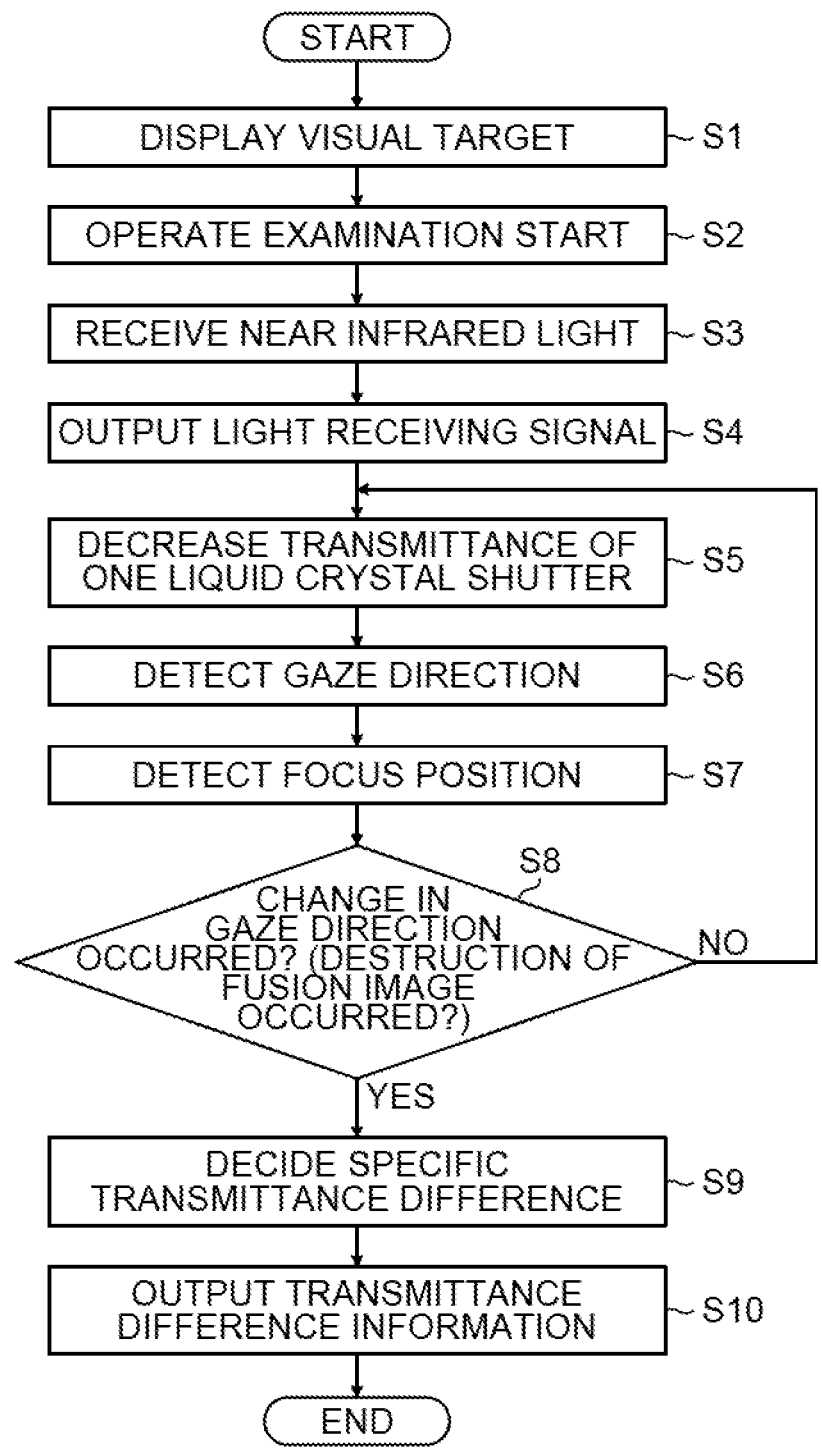
FIG. 10 is a flowchart illustrating a flow of examination of eye fatigue of the subject's eye by the eye-fatigue examining device.

Next, the operation of the eye-fatigue examining device 10 having the above configuration will be described with reference to FIG. 10. FIG. 10 is a flow chart illustrating a flow of an eye fatigue examination (eye-fatigue examining method) for the subject's eyes 9R, 9L by the eye-fatigue examining device 10.

After a patient places a chin on the face receiving part (not shown) of the optometric table 11 and puts a forehead, an optometrist causes the visual target displaying unit 13 to display the visual target (Step S1, corresponding to the visual target displaying step in the present invention). As a result, the subject's eyes 9R and 9L of the patient visually observe (natural vision) the examination visual target 19 through the dichroic mirrors 14R, 14L, respectively. Next, the optometrist performs an operation for stating examination with an operating unit (not shown) of the eye-fatigue examining device 10 (Step S2).

When the examination starting operation is performed, near infrared lights having a wavelength of 950 nm are emitted from the infrared light sources 12R, 12L to the subject's eyes 9R, 9L. In addition, near infrared lights having a wavelength of 840 nm are emitted from the semiconductor elements 40 of the measuring units 16R, 16L. The near infrared lights having a wavelength of 840 nm respectively enter the subject's eyes 9R, 9L through the collimator lenses 41, the beam splitters 42, the mirrors 32, the dichroic mirrors 31, the objective lenses 30, and the dichroic mirrors 14R, 14L. As a result, the near infrared lights of two wavelengths enter the subject's eyes 9R, 9L (Step S3).

The near infrared lights of two wavelengths incident on the subject's eyes 9R, 9L are reflected by the subject's eyes 9R, 9L, then pass through the optical paths 21R, 21L and the dichroic mirrors 14R, 14L and enter the objective lenses 30 of the measuring units 16R, 16L, respectively. By arranging the dichroic mirrors 14R, 14L that transmit visible light and reflect near infrared light on the optical paths 21R, 21L in this manner, the eye fatigue can be objectively examined without giving sense of incongruity to the patient while maintaining a state where the subject's eyes 9R, 9L visually observe (natural vision: with both eyes open) the examination visual target 19.

The near infrared light having a wavelength of 950 nm incident on the objective lens 30 is received by the imaging device 37 through the dichroic mirror 31, the relay lens 35, and the imaging lens 36, and a light receiving signal is outputted from the imaging device 37 to the examining device main body 17. Further, the near infrared light having a wavelength of 950 nm incident on the objective lens 30 is received by the imaging device 46 through the dichroic mirror 31, the mirror 32, the beam splitter 42, the mirror 43, the imaging lens 44, and the Hartmann plate 45, and the light receiving signal is outputted from the imaging device 46 to the examining device main body 17 (Step S4).

Next, the transmittance adjusting unit 50 continuously or stepwise decreases the transmittance corresponding to one of the transmitting areas 23R, 23L of the liquid crystal shutters 15R, 15L with the lapse of time, and maintains the transmittance corresponding to the other of the transmitting areas 23R and 23L of the liquid crystal shutters 15R, 15L constant (for example, maximum transmittance). As a result, the transmittance difference between the transmitting areas 23R, 23L continuously or stepwise increases with the lapse of time (Step S5, corresponding to the light quantity difference adjusting step of the present invention). As a result, the light quantity difference between visible lights respectively incident on the subject's eyes 9R, 9L also increases continuously or stepwise.

Here, if it is intended to simply increase the light quantity difference between visible lights respectively incident on the subject's eyes 9R, 9L, for example, a method using a Bagolini red filter bar (hereinafter simply abbreviated as BRFB) used for subjective examination such as strabismus and heterophoria can be considered. However, in the subjective examination method using BRFB, the examination result varies depending on procedure by the optometrist. Also, since BRFB is worn on one eye, the fusion image may be destroyed at the time of the first filter of BRFB being worn. Further, since the filter transmittance of the BRFB does not change in an arithmetic manner, the above-mentioned specific transmittance difference cannot be accurately obtained. Therefore, with a subjective examination method using BRFB, accurate examination of eye fatigue cannot be performed.

On the other hand, in the present embodiment, continuous or stepwise increase in the transmittance difference between the transmitting areas 23R, 23L can be performed with automatic control by the transmittance adjusting unit 50, so that accurate examination can be performed by eliminating errors due to procedure of the optometrist. Further, at the start of the examination, the transmittance difference between the transmitting areas 23R, 23L can be made zero, so that the fusion image is prevented from being destroyed at the start of the examination. In addition, since the transmittance difference between the transmitting areas 23R, 23L can be changed in an arithmetic manner, the above-described specific transmittance difference can be accurately obtained.

When the transmittance adjusting unit 50 starts increasing the transmittance difference, the gaze direction detecting unit 51 starts the detection of the gaze directions of the subject's eyes 9R, 9L. The gaze direction detecting unit 51 uses the image measuring method described with reference to FIGS. 7 and 8 described above, to detect the gaze directions of the subject's eyes 9R, 9L, based on the light receiving signals input from the imaging device 37 of both the anterior eye segment observing systems 25 of the measuring units 16R, 16L (Step S6, corresponding to the gaze direction detecting step of the present invention). Then, the gaze direction detecting unit 51 outputs the detection results of the gaze directions of the subject's eyes 9R, 9L to the determining unit 53.

At the same time, the focus position detecting unit 52 starts the detection of the focus positions of the subject's eyes 9R, 9L. The focus position detecting unit 52 measures the wavefront aberrations of the subject's eyes 9R, 9L based on the light receiving signals input from the imaging devices 46 of both the aberration measuring systems 26 for both the measuring units 16R, 16L, and detects the focus positions of the subject's eyes 9R, 9L based on the measuring results of the wavefront aberrations (Step S7). Then, the focus position detecting unit 52 outputs the detection results of the focus positions of the subject's eyes 9R, 9L to the determining unit 53.

Based on the gaze direction detection results input from the gaze direction detecting unit 51 and the focus position detection result input from the focus position detecting unit 52, the determining unit 53 determines the presence or absence of a change in the gaze directions (positions of the pupils, positions of the Purkinje images 59p) from a state in which the subject's eyes 9R, 9L visually observe the visual target (Step S8). At this time, by using the focus position detection results of the subject's eyes 9R, 9L for determining the presence or absence of a change in the gaze directions, the accuracy of the determination can be improved as described above.

Hereinafter, the processing from Step S5 to Step S8 described above is repeatedly executed (NO in Step S8) until the determining unit 53 determines that there is a change in the gaze directions. As a result, the transmittance difference between the transmitting areas 23R, 23L increases with the lapse of time, so that the light quantity difference between visible lights respectively incident on the subject's eyes 9R, 9L increases with the lapse of time. Then, as illustrated in Parts (A) to (C) in FIG. 9 described above, when the transmittance difference (light quantity difference) between the transmitting areas 23R, 23L increases beyond a certain range, the patient can not recognize the image of the examination visual target 19 respectively visually observed by the subject's eyes 9R, 9L, as one image and the fusion image is destroyed. As a result, a change in the gaze directions of the subject's eyes 9R, 9L due to increase in the transmittance difference (light quantity difference) occurs, and this change is detected by the determining unit 53.

When the determining unit 53 determines that a change in the gaze directions of the subject's eyes 9R, 9L due to the increase (destruction of the fusion image) of the transmittance difference has occurred (YES in Step S8), the transmittance difference determining unit 54 obtains the transmittances of the transmitting areas 23R, 23L at the time when a change in the gaze directions occurs from the transmittance adjusting unit 50. As a result, the transmittance difference determining unit 54 determines a specific transmittance difference (Step S9, corresponding to the light quantity difference deciding step of the present invention). Then, the transmittance difference determining unit 54 outputs transmittance difference information indicating the decided specific transmittance difference to the outputting unit 55.

Upon receiving the input of the transmittance difference information from the transmittance difference determining unit 54, the outputting unit 55 respectively outputs the transmittance difference information to the displaying unit 56 and the storing unit 57 as an index indicating eye fatigue of the subject's eyes 9R, 9L (Step S10, corresponding to the outputting step of the present invention). As a result, the transmittance difference information is displayed on the displaying unit 56 and stored in the storing unit 57, so that a doctor can diagnose and evaluate eye fatigue of the subject's eyes 9R, 9L of the patient, based on the displayed or stored transmittance difference information.

Advantageous Effect of Present Embodiment

As described above, in the present embodiment, a change in the gaze directions of the subject's eyes 9R, 9L due to the increase in the transmittance difference between the transmitting areas 23R, 23L is detected, and the difference in transmittance at the time of detection is obtained as an index indicating eye fatigue of the subject's eyes 9R, 9L. Therefore, eye fatigue of the subject's eyes 9R, 9L can be objectively examined (evaluated) based on the fusional faculty of the patient. Since the fusion image is visual function which is hardly influenced by aging, eye fatigue of the subject's eyes 9R, 9L can be examined regardless of the age of the patient. As a result, it is possible to examine the eye fatigue of the middle-aged and elderly age group for which anything has not been done conventionally.

That is, clinically, an objective examination (evaluation) method useful for diagnosis and treatment of the CVS can be performed by measuring eye fatigue of the middle-aged and elderly age group. In addition, it is possible to decide an optimum power lens that hardly causes eye fatigue most when an adult of a middle-aged and elderly age group uses the VDT terminal. Further, it is possible to develop less fatigue eyeglass lenses, or develop 3D displays because examination (evaluation) of eye fatigue is made possible.

Further, in the present embodiment, it is possible to automatically increase continuously or stepwise (arithmetically) the transmittance difference between the transmitting areas 23R, 23L, so that accurate examination of eye fatigue of subject's eyes 9R, 9L becomes possible.

Further, in the present embodiment, because the dichroic mirrors 14R, 14L that transmit visible light and reflect near infrared light (measuring light) are respectively arranged on the optical paths 21R, 21L, it is possible to examine eye fatigue of the subject's eyes 9R, 9L while the patient is in a natural state of visually observing the examination visual target 19 (natural vision).

Second Embodiment

In the first embodiment, the dichroic mirrors 14R, 14L are respectively arranged on the optical paths 21R, 21L, but one dichroic mirror 60 (see FIG. 11 and FIG. 12) may be arranged to stride over the two optical paths 21R, 21L.

Figure 11:
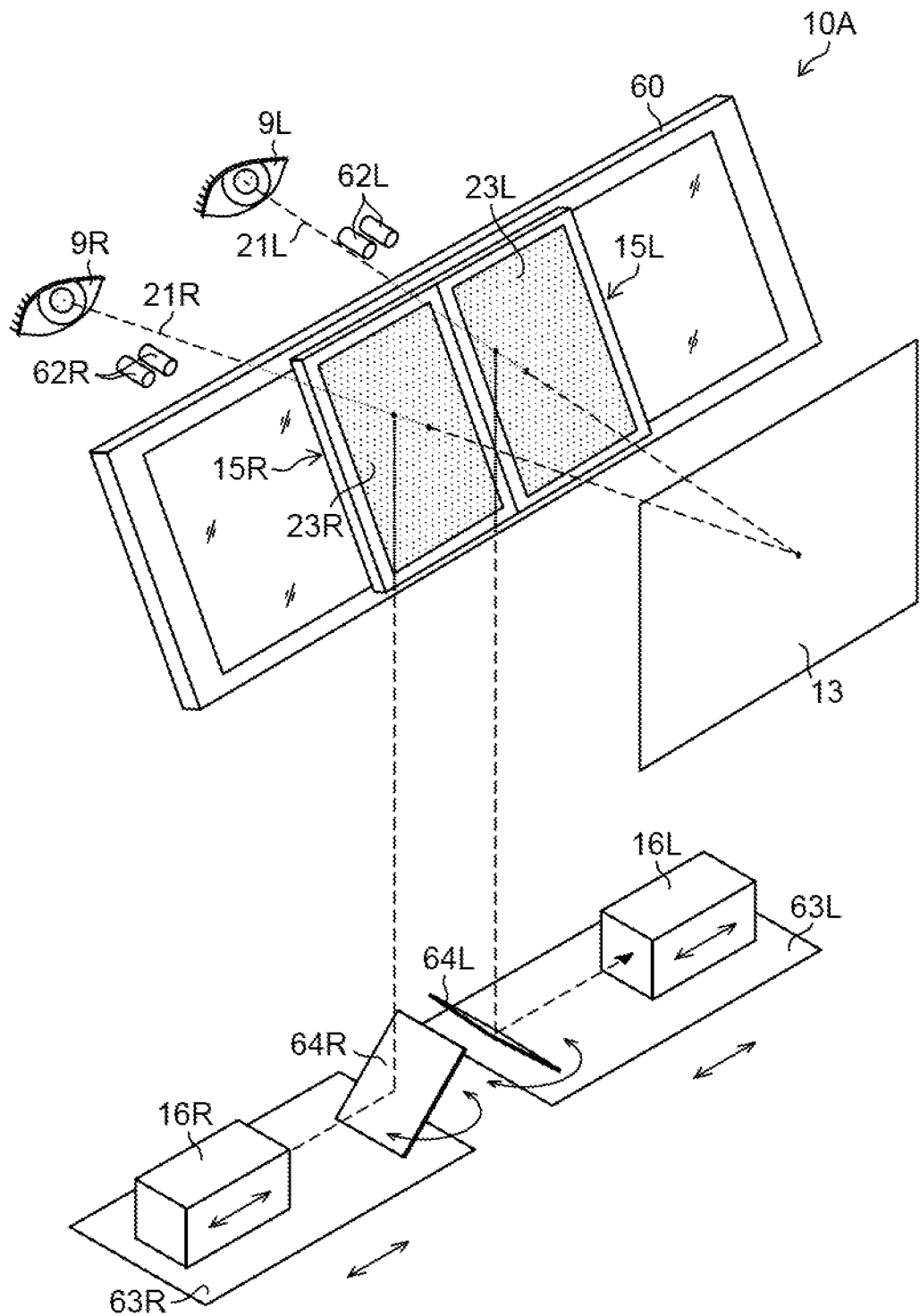
FIG. 11 is a perspective view illustrating a schematic configuration of an eye-fatigue examining device according to a second embodiment.
Figure 12:
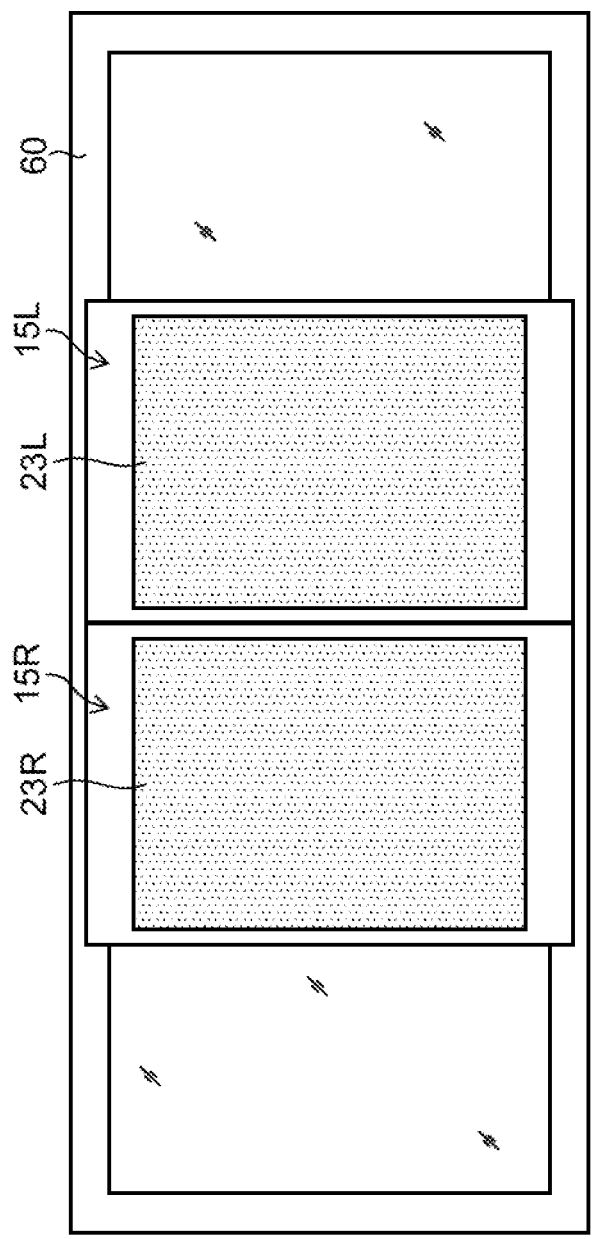
FIG. 12 is a front view of a dichroic mirror as viewed from a side of a visual target displaying unit.

FIG. 11 is a perspective view illustrating a schematic configuration of an eye-fatigue examining device 10A according to a second embodiment including one dichroic mirror 60 instead of the dichroic mirrors 14R, 14L. FIG. 12 is a front view of the dichroic mirror 60 as viewed from a side of the visual target displaying unit 13.

The eye-fatigue examining device 10A has basically the same configuration as the eye-fatigue examining device 10 of the above first embodiment, except that the eye-fatigue examining device 10A includes the dichroic mirror 60, stereo cameras 62R, 62L, unit support bases 63R, 63L, and the mirrors 64R, 64L. Therefore, elements identical in function or configuration with those in the above first embodiment are designated by the same reference numerals or characters, and description thereof is omitted.

The dichroic mirror 60 is arranged to stride over (across) the optical paths 21R, 21L in a state where the dichroic mirror 60 is inclined downward by 45 degrees with respect to the optical paths 21R, 21L. Like the dichroic mirrors 14R, 14L of the above first embodiment, the dichroic mirror 60 transmits visible light (light in the first wavelength band of the present invention) and reflects near infrared light (light in the second wavelength band of the present invention). As a result, the examination visual target 19 can be visually observed (natural vision) by the subject's eyes 9R, 9L.

In addition, the dichroic mirror 60 reflects the near infrared lights traveling along the optical paths 21R, 21L among the near infrared lights respectively reflected by the subject's eyes 9R, 9L toward lower sides of the optical paths 21R, 21L, respectively.

The above-mentioned liquid crystal shutters 15R, 15L are attached on a surface of the dichroic mirror 60 on the side of the visual target displaying unit 13. The liquid crystal shutters 15R, 15L are attached to the dichroic mirror 60 so as to be positioned on the optical paths 21R, 21L, respectively. Thus, by increasing the transmittance difference between the transmitting areas 23R, 23L of the liquid crystal shutters 15R, 15L by the above-mentioned transmittance adjusting unit 50 (see FIG. 5), similarly to the above first embodiment, it is possible to increase the light quantity difference between visible lights incident on the subject's eyes 9R, 9L.

The stereo cameras 62R, 62L constitute a part of the gaze direction detecting unit of the present invention. Instead of the infrared light sources 12R, 12L (see FIG. 1) of the above first embodiment, the stereo cameras 62R, 62L are attached to the above-mentioned face receiving part (not shown). The stereo cameras 62R, 62L respectively image the subject's eyes 9R, 9L from two directions at the same time to generate stereoscopic imaging signals, and respectively output the stereoscopic imaging signals of the respective subject's eyes 9R, 9L to the gaze direction detecting unit 51 (see FIG. 5).

The gaze direction detecting unit 51 of the second embodiment analyzes the stereoscopic imaging signal of each of the subject's eyes 9R, 9L, respectively input from the stereo cameras 62R, 62L and detects the gaze directions of the subject's eyes 9R, 9L. The method of detecting the gaze directions of the subject's eyes 9R, 9L from the stereoscopic imaging signals obtained by stereoscopically imaging the subject's eyes 9R, 9L is a well-known technique, therefore, the detailed description about the technique will be omitted.

The unit support bases 63R and 63L are arranged below the dichroic mirror 60. A mirror 64R and a measuring unit 16R are arranged on the unit support base 63R, and a mirror 64L and a measuring unit 16L are arranged on the unit support base 63L. Positions of the unit support bases 63R, 63L can be adjusted in a direction parallel to an eye width direction of the subject's eyes 9R, 9L. As a result, the near infrared lights reflected to lower sides of the optical paths 21R, 21L by the dichroic mirror 60 are respectively made incident on the mirrors 64R, 64L.

The mirror 64R reflects the near infrared light reflected to the lower side of the optical path 21R by the dichroic mirror 60 toward the measuring unit 16R. Further, the mirror 64L reflects the near infrared light reflected to the lower side of the optical path 21L by the dichroic mirror 60 toward the measuring unit 16L. The mirrors 64R, 64L can be rotationally adjusted around an axis perpendicular to upper surfaces of the unit support bases 63R, 63L.

The measuring units 16R, 16L of the second embodiment have a configuration in which the anterior eye segment observing system 25 is mainly omitted from the measuring units 16R, 16L of the above first embodiment illustrated in FIG. 4. The measuring units 16R, 16L emit near infrared lights having a wavelength of 840 nm toward the mirrors 64R, 64L. As a result, the near infrared lights having a wavelength of 840 nm are respectively incident on the subject's eyes 9R, 9L through the mirrors 64R, 64L and the dichroic mirror 60. Then, the near infrared lights having the wavelength of 840 nm reflected by the subject's eyes 9R, 9L are respectively incident on the measuring units 16R, 16L through the optical paths 21R, 21L, the dichroic mirror 60, and the mirrors 64R, 64L.

The aberration measuring systems 26 (see FIG. 4) of the measuring units 16R, 16L respectively receive the near infrared lights having a wavelength of 840 nm reflected by the subject's eyes 9R, 9L, as in the above first embodiment, and output light receiving signals indicating a plurality of point images to the examining device main body 17.

The examining device main body 17 of the second embodiment basically has the same configuration as the examining device main body 17 of the above first embodiment except that the gaze direction detection method by the gaze direction detecting unit 51 is different, so that a detailed explanation will be omitted.

As described above, also in the eye-fatigue examining device 10A of the second embodiment, in a state where the patient visually observes (natural vision) the examination visual target 19 through the dichroic mirror 60, it is possible to detect a change in the gaze directions of the subject's eyes 9R, 9L due to the increase in the transmittance difference (destruction of the fusion image) between the transmitting areas 23R and 23L. As a result, the same effect as the eye-fatigue examining device 10 of the above first embodiment can be obtained.

Third Embodiment

In the above first embodiment and the above second embodiment, the liquid crystal shutters 15R, 15L are arranged on the optical paths 21R, 21L, respectively, but one liquid crystal shutter 70 (see FIG. 13) may be arranged to stride over the two optical paths 21R, 21L.

Figure 13:
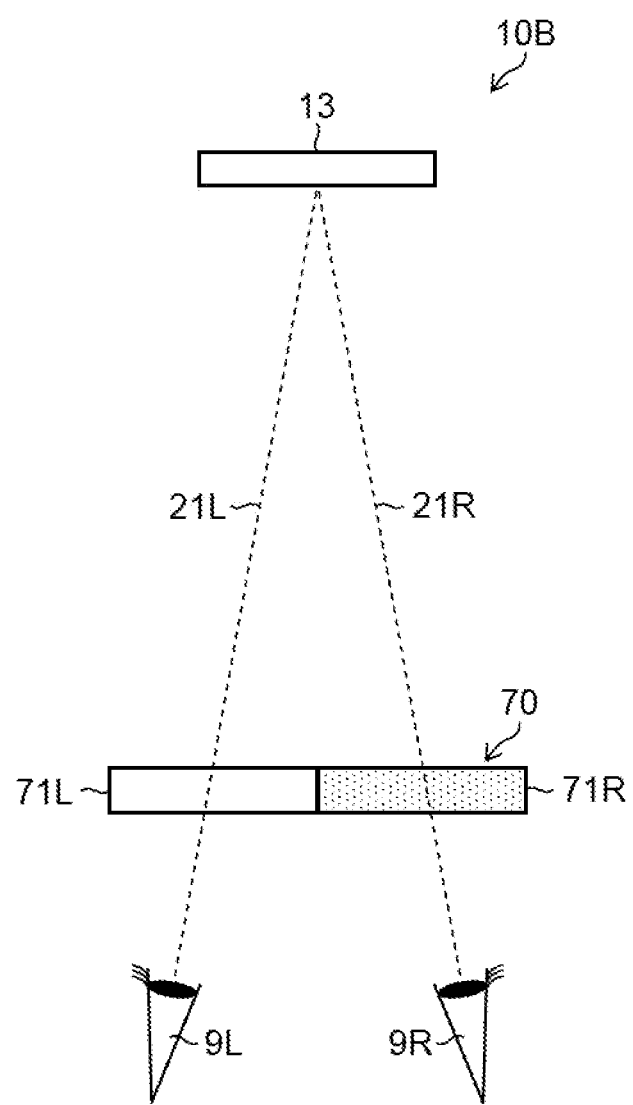
FIG. 13 is a top view illustrating a schematic configuration of an eye-fatigue examining device according to a third embodiment.

FIG. 13 is a top view illustrating a schematic configuration of an eye-fatigue examining device 10B according to a third embodiment which includes the liquid crystal shutter 70 instead of the liquid crystal shutters 15R, 15L. In FIG. 13, illustration of the other parts than the visual target displaying unit 13 and the liquid crystal shutter 70 is omitted. The eye-fatigue examining device 10B basically has the same configuration as the eye-fatigue examining device 10 according to the above first embodiment or the eye-fatigue examining device 10A according to the above second embodiment, except that the liquid crystal shutter 70 is provided.

The liquid crystal shutter 70 constitutes a part of the light quantity difference adjusting unit of the present invention, and is arranged to stride over (across) the optical paths 21R, 21L. The liquid crystal shutter 70 can adjust the light transmittance for each liquid crystal pixel. The liquid crystal shutter 70 has a transmitting area 71R through which visible light passing through the optical path 21R transmits, and a transmitting area 71L through which visible light passing through the optical path 21L transmits.

The transmittances of the transmitting areas 71R, 71L are adjusted by the transmittance adjusting unit 50 (see FIG. 5). Accordingly, by decreasing the transmittance of one of the transmitting areas 71R and 71L and maintaining the transmittance of the other constant, it is possible to increase the transmittance difference between the transmitting areas 71R, 71L. As a result, similarly to each of the above-described embodiments, it is possible to increase the light quantity difference between visible lights respectively incident on the subject's eyes 9R, 9L.

As described above, the eye-fatigue examining device 10B according to the third embodiment basically has the same configuration as the eye-fatigue examining device 10, 10A of the respective embodiments, except that the liquid crystal shutter 70 is different from the liquid crystal shutters 15R, 15L of the embodiments. Therefore, the same effects as in each of the above embodiments can be obtained.

Others

In each of the above embodiments, the liquid crystal shutters 15R, 15L, and 70 are used to increase the light quantity difference between visible lights respectively incident on the subject's eyes 9R, 9L. However, instead of the liquid crystal shutter, various devices or members capable of adjusting (reducing) the light transmittance such as a variable density filter, a liquid shutter, an ND (Neutral Density) filter, or the like may be used.

Figure 14:
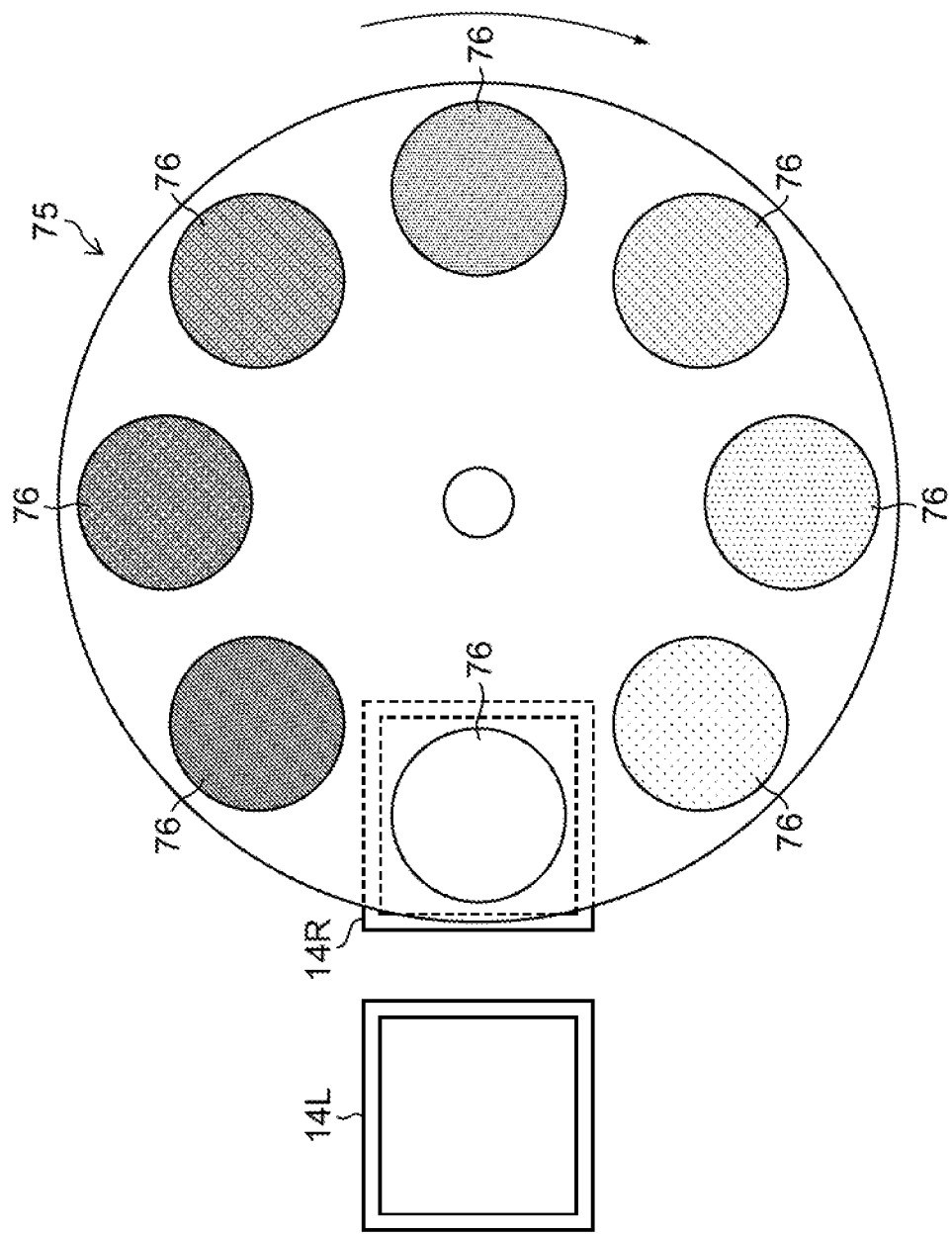
FIG. 14 is a schematic diagram of another embodiment for increasing a difference in light quantity between visible lights respectively incident on the subject's eyes using a plurality of ND filters provided in a turret.

FIG. 14 is a schematic diagram of another embodiment for increasing the light quantity difference between visible lights respectively incident on the subject's eyes 9R, 9L, by using a plurality of ND filters 76 provided in a turret 75. As illustrated in FIG. 14, the turret 75 is provided between the dichroic mirrors 14R, 14L (which may be the dichroic mirror 60 illustrated in FIG. 11) and the visual target displaying unit 13. The turret 75 is provided with a plurality of ND filters 76 along a circumferential direction of the turret 75. The ND filters 76 have transmittances (densities) of visible light stepwisely varied.

The turret 75, by rotation about its rotation axis, inserts the plurality of ND filters 76 into one of the optical paths 21R, 21L (the optical path 21R in FIG. 14) in order from the one having the highest transmittance. As a result, the light quantity of visible light incident on the subject's eye 9R decreases stepwise and the light quantity of visible light incident on the subject's eye 9L is maintained constant. Therefore, it is possible to increase the light quantity difference between visible lights respectively incident on the subject's eyes 9R, 9L.

When a variable density filter is used, it is sufficient only to replace the liquid crystal shutters 15R, 15L with variable density filters, therefore the detailed description thereof will be omitted.

In each of the above embodiments, the liquid crystal shutters 15R, 15L, 70 are arranged at positions distant from (apart from) the subject's eyes 9R, 9L. However, for example, the liquid crystal shutters 15R, 15L and the like may be provided in a frame of a goggle, or in a frame of eyeglass lenses worn by a patient to increase the light quantity difference between visible lights respectively incident on the subject's eyes 9R, 9L.

In the above first embodiment and the above second embodiment, the liquid crystal shutters 15R, 15L are arranged on the optical paths 21R, 21L, respectively, but the liquid crystal shutter may be arranged only in one of the optical paths 21R, 21L to increase the light quantity difference between visible lights respectively incident on the subject's eyes 9R, 9L.

In each of the above embodiments, as described above, the focus positions of the subject's eyes 9R, 9L are detected by the aberration measuring systems 26 and the focus position detecting unit 52 to improve the accuracy of determination by the determining unit 53, but detection of this focus position may be omitted.

In each of the above embodiments, the gaze direction and the focus position of the subject's eye 9R, and the gaze direction and the focus position of the subject's eye 9L are simultaneously detected by the two measuring units 16R and 16L, but the detection of the gaze direction and the focus position of the subject's eye 9R and the detection of the gaze direction and the focus position of the subject's eye 9L may be alternately performed by one measuring unit while switching the detections for subject's eyes 9R, 9L at high speed.

In each of the above embodiments, the gaze directions and the focus positions of the subject's eyes 9R, 9L are detected by using near infrared lights having a wavelength of 950 nm and a wavelength of 840 nm, as light in the second wavelength band of the present invention, but the gaze direction and the focus position may be detected using light in other wavelength band which does not affect the eyes.

In each of the above embodiments, by decreasing the light quantity of visible light incident on one of the subject's eyes 9R, 9L and maintaining the light quantity of visible light incident on the other of the subject's eyes 9R, 9L constant, the light quantity difference between visible lights respectively incident on the subject's eyes 9R, 9L is increased. However, the method of adjusting the quantity of light incident on one and the other of the subject's eyes 9R, 9L is not particularly limited as long as it is possible to increase the light quantity difference.

REFERENCE SIGNS LIST 10, 10A, 10B Eye-fatigue examining device, 12R, 12L infrared light source, 13 visual target displaying unit, 14R, 14L, 60 dichroic mirror, 15R, 15L, 70 liquid crystal shutter, 16R, 16L measuring unit, 17 examining device main body, 19 examination visual target, 21R, 21L optical path, 23R, 23L, 71R, 71L transmitting area, 25 anterior eye segment observing system, 26 aberration measuring system, 50 transmittance adjusting unit, 51 gaze direction detecting unit, 52 focus position detecting unit, 53 determining unit, 54 transmittance difference determining unit, 55 outputting unit, 62R, 62L stereo camera, 75 turret.

The invention claimed is:

1. An eye-fatigue examining device comprising:
processing circuitry configured to control liquid crystal shutters to increase a light quantity difference between lights respectively incident on right and left subject's eyes;
the processing circuitry further configured to detect gaze directions of the respective subject's eyes while controlling the liquid crystal shutters to increase the light quantity difference; and
the processing circuitry further configured to decide a specific light quantity difference at which a change in the gaze directions due to an increase in the light quantity difference occurs, based on the detected gaze directions of the respective subject's eyes detected by the processing circuitry,
wherein the processing circuitry is further configured to output the decided specific light quantity difference as an index of eye fatigue of the subject's eyes.

2. The eye-fatigue examining device according to claim 1, comprising a visual target display configured to display an examination visual target to be visually observed by the subject's eyes,
wherein the processing circuitry decides the specific light quantity difference, by determining presence or absence of a change in the gaze directions from a state in which the subject's eyes visually observe the examination visual target based on the detected gaze direction.

3. The eye-fatigue examining device according to claim 2, wherein the processing circuitry detects positions of Purkinje images of the subject's eyes or positions of pupils of the subject's eyes, and
the processing circuitry decides the specific light quantity difference, by determining presence or absence of a change in the positions of the Purkinje images or the pupils from a state in which the subject's eyes visually observe the examination visual target.

4. The eye-fatigue examining device according to claim 1, wherein the processing circuitry increases the light quantity difference, by decreasing a light quantity of a light incident on one of the subject's eyes and maintaining a light quantity of a light incident on the other of the subject's eyes constant.

5. The eye-fatigue examining device according claim 1, wherein the liquid crystal shutters include a transmitting area which can adjust a transmittance of the light incident on at least one of the subject's eyes, and processing circuitry increases the light quantity difference by adjusting the transmittance of the transmitting area.

6. The eye-fatigue examining device according to claim 5, wherein, when the liquid crystal shutters have the transmitting area on an optical path of the light incident on each of the subject's eyes, the specific light quantity difference decided by the processing circuitry is expressed as a difference in the transmittance between the two transmitting areas.

7. The eye-fatigue examining device according to claim 1, wherein the processing circuitry continuously or stepwise increases the light quantity difference.

8. The eye-fatigue examining device according to claim 1, wherein the lights incident on the subject's eyes include a light in a first wavelength band and a light in a second wavelength band different from the first wavelength band,
a dichroic mirror is provided on optical paths of the lights reflected by the subject's eyes, the dichroic mirror configured to transmit the light in the first wavelength band and reflect the light in the second wavelength band reflected by the subject's eyes to a side of the optical paths, and
the processing circuitry detects the gaze directions based on a result of detecting the light in the second wavelength band reflected by the dichroic mirror.

9. An eye-fatigue examining method comprising:
a light quantity difference adjusting step of increasing a light quantity difference between lights respectively incident on right and left subject's eyes;
a gaze direction detecting step of detecting gaze directions of the respective subject's eyes while the light quantity difference is increased in the light quantity difference adjusting step;
a light quantity difference deciding step of deciding a specific light quantity difference at which a change in the gaze directions due to an increase in the light quantity difference occurs, based on a detection result of the gaze direction detecting step; and
an outputting step of outputting the specific light quantity difference decided in the light quantity difference deciding step as an index of eye fatigue of the subject's eyes.

10. The eye-fatigue examining method according to claim 9, comprising
a visual target displaying step of displaying an examination visual target to be visually observed by the subject's eyes,
wherein in the light quantity difference deciding step, the specific light quantity difference is decided, by determining presence or absence of a change in the gaze directions from a state in which the subject's eyes visually observe the examination visual target based on the detection result in the gaze direction detecting step.

11. The eye-fatigue examining method according to claim 10,
wherein in the gaze direction detecting step, positions of Purkinje images of the subject's eyes or positions of pupils of the subject's eyes are detected, and
in the light quantity difference deciding step, the specific light quantity difference is decided by determining presence or absence of a change of the positions of the Purkinje images or the pupils from a state in which the subject's eyes visually observe the examination visual target.

12. The eye-fatigue examining method according to claim 9,
wherein in the light quantity difference adjusting step, the light quantity difference is increased, by decreasing a light quantity of a light incident on one of the subject's eyes and maintaining a light quantity of a light incident on the other of the subject's eyes constant.

13. The eye-fatigue examining method according to claim 9, comprising
arranging a transmitting area which can adjust a transmittance of a light, on an optical path of the light incident on at least one of the subject's eyes,
wherein, in the light quantity difference adjusting step, the light quantity difference is increased by adjusting the transmittance of the transmitting area.

14. The eye-fatigue examining method according to claim 13,
wherein when the transmitting area is arranged on an optical path of the light incident on each of the subject's eyes, the specific light quantity difference decided in the light quantity difference deciding step is expressed as a difference in the transmittance between the two transmitting areas.

15. The eye-fatigue examining method according to claim 9,
wherein in the light quantity difference adjusting step, the light quantity difference is continuously or stepwise increased.

16. The eye-fatigue examining method according to claim 9,
wherein the lights incident on the subject's eyes include a light in a first wavelength band and a light in a second wavelength band different from the first wavelength band,
a dichroic mirror is arranged on optical paths of the lights reflected by the subject's eyes, the dichroic mirror configured to transmit the light in the first wavelength band and reflect the light in the second wavelength band reflected by the subject's eyes to a side of the optical paths, and
in the gaze direction detecting step, the gaze directions are detected based on a result of detecting the light in the second wavelength band reflected by the dichroic mirror.

* * * * *